US012560263B2

(12) United States Patent
Andrews et al.

(10) Patent No.: US 12,560,263 B2
(45) Date of Patent: ***Feb. 24, 2026

(54) ASEPTIC COUPLING DEVICES

(71) Applicant: Colder Products Company, Roseville, MN (US)

(72) Inventors: Todd C. Andrews, River Falls, WI (US); Patrick T. Gerst, Oakdale, MN (US); Jeremy H. Nichols, Maple Grove, MN (US); Randall S. Williams, Minneapolis, MN (US)

(73) Assignee: Colder Products Company, Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/798,200

(22) Filed: Aug. 8, 2024

(65) Prior Publication Data

US 2025/0043894 A1     Feb. 6, 2025

Related U.S. Application Data

(63) Continuation of application No. 17/111,921, filed on Dec. 4, 2020, now Pat. No. 12,060,960, which is a
(Continued)

(51) Int. Cl.
A61M 39/18        (2006.01)
A61M 39/20        (2006.01)
(Continued)

(52) U.S. Cl.
CPC ............. F16L 37/00 (2013.01); A61M 39/18 (2013.01); A61M 39/20 (2013.01); F16L 37/113 (2013.01);
(Continued)

(58) Field of Classification Search
CPC ......... F16L 37/00; F16L 37/24; F16L 37/244; F16L 37/248; F16L 2201/40;
(Continued)

(56) References Cited

U.S. PATENT DOCUMENTS 913,144 A     2/1909   James et al.
1,947,593 A     2/1934   Hamilton
(Continued)

FOREIGN PATENT DOCUMENTS

CN           1115965 A      1/1996
DE            2427381       7/1975
WO      WO 20061117138     11/2006

OTHER PUBLICATIONS

International Search Report and Written Report in PCT Appln US/2010/027311, dated Aug. 6, 2010, 13 pages.

*Primary Examiner* — Aaron M Dunwoody
(74) *Attorney, Agent, or Firm* — Fish & Richardson P.C.

(57)        ABSTRACT

Formation of a sterile connection includes inserting a first aseptic coupling device into a second aseptic coupling device, removing a first membrane from the first aseptic coupling device and a second membrane from the second aseptic coupling device, and rotating a locking clip on the first aseptic coupling device to compress a first seal member of the first aseptic coupling device with a second seal member of the second aseptic coupling device to form a sterile fluid passageway.

16 Claims, 34 Drawing Sheets

Related U.S. Application Data continuation of application No. 15/421,836, filed on Feb. 1, 2017, now Pat. No. 10,871,250, which is a continuation of application No. 14/683,662, filed on Apr. 10, 2015, now Pat. No. 9,879,808, which is a continuation of application No. 13/693,720, filed on Dec. 4, 2012, now Pat. No. 9,027,968, which is a continuation of application No. 12/724,125, filed on Mar. 15, 2010, now Pat. No. 8,491,016.

(60) Provisional application No. 61/160,603, filed on Mar. 16, 2009.

(51) Int. Cl.
  *F16L 37/00*     (2006.01)
  *F16L 37/113*    (2006.01)
  *F16L 37/30*     (2006.01)

(52) U.S. Cl.
  CPC ........... *F16L 37/30* (2013.01); *F16L 2201/44* (2013.01); *Y10T 29/49826* (2015.01)

(58) Field of Classification Search
  CPC ....... F16L 2201/44; A61M 2039/0285; A61M 2039/0288; A61M 39/18; A61M 39/20; A61M 39/167
  See application file for complete search history.

(56) References Cited

U.S. PATENT DOCUMENTS

| | | | |
|---|---|---|---|
| 2,419,702 | A | 4/1947 | Barnes |
| 2,868,563 | A | 1/1959 | Wood |
| 3,758,137 | A | 9/1973 | Kershaw |
| 3,831,984 | A | 8/1974 | Kutina et al. |
| 3,900,223 | A | 8/1975 | Schafer |
| 3,909,910 | A | 10/1975 | Rowe et al. |
| 4,019,512 | A | 4/1977 | Tenczar |
| 4,022,205 | A | 5/1977 | Tenczar |
| 4,022,496 | A | 5/1977 | Crissy |
| 4,187,846 | A | 2/1980 | Lolachi et al. |
| 4,418,945 | A | 12/1983 | Kellogg |
| 4,610,469 | A | 9/1986 | Wolff-Mooij |
| 4,621,841 | A | 11/1986 | Wakefield |
| 4,673,400 | A | 6/1987 | Martin |
| 4,738,401 | A | 4/1988 | Fillcicchia |
| 4,886,303 | A | 12/1989 | Carson et al. |
| 4,951,326 | A | 8/1990 | Barnes et al. |
| 5,316,351 | A | 5/1994 | Czimny et al. |
| 5,348,570 | A | 9/1994 | Ruppert et al. |
| 5,492,147 | A | 2/1996 | Challender |
| 5,494,074 | A | 2/1996 | Ramacier |
| 6,050,613 | A | 4/2000 | Wartluft |
| 6,655,655 | B1 * | 12/2003 | Matkovich ......... A61M 39/1011 |
| | | | 604/905 |
| 6,679,529 | B2 | 1/2004 | Johnson et al. |
| 6,911,025 | B2 | 6/2005 | Miyahara |
| 7,083,605 | B2 | 8/2006 | Miyahara |
| 7,523,918 | B2 | 4/2009 | Matkovich et al. |
| 7,628,772 | B2 | 12/2009 | McConnell et al. |
| 7,628,782 | B2 | 12/2009 | Adair et al. |
| 7,918,243 | B2 | 4/2011 | Diodati et al. |
| 8,586,045 | B2 | 11/2013 | Zeller et al. |
| 9,364,653 | B2 | 6/2016 | Williams et al. |
| 2002/0093192 | A1 | 7/2002 | Matkovich |
| 2003/0030272 | A1 * | 2/2003 | Johnson ................. F16L 29/00 |
| | | | 285/70 |
| 2004/0168690 | A1 | 9/2004 | Payne |
| 2006/0138069 | A1 | 6/2006 | Domkowski et al. |
| 2006/0252298 | A1 | 11/2006 | Biddel et al. |
| 2007/0001459 | A1 | 1/2007 | Wells |
| 2007/0027437 | A1 | 2/2007 | Burg et al. |
| 2009/0050213 | A1 | 2/2009 | Biddell et al. |
| 2009/0275888 | A1 | 11/2009 | Kriesel |
| 2010/0230950 | A1 | 9/2010 | Williams et al. |
| 2010/0292673 | A1 | 11/2010 | Korogi et al. |
| 2011/0061761 | A1 | 3/2011 | Muehlemann |
| 2013/0197485 | A1 | 8/2013 | Gardner et al. |
| 2013/0207380 | A1 | 8/2013 | Williams et al. |
| 2013/0289517 | A1 | 10/2013 | Williams et al. |
| 2014/0358115 | A1 | 12/2014 | Chelak et al. |
| 2015/0314120 | A1 | 11/2015 | Gardner |
| 2016/0053927 | A1 | 2/2016 | Whitaker |
| 2017/0284584 | A1 | 10/2017 | Kesselaar et al. |
| 2018/0264251 | A1 | 9/2018 | Lofving |
| 2018/0304067 | A1 | 10/2018 | Ryan |

* cited by examiner

ASEPTIC COUPLING DEVICES

RELATED APPLICATIONS

This application is a continuation of U.S. patent application Ser. No. 17/111,921 (U.S. Pat. No. 12,060,960) filed Dec. 4, 2020, which is a continuation of U.S. patent application Ser. No. 15/421,836 (U.S. Pat. No. 10,871,250) filed Feb. 1, 2017, which is a continuation of U.S. patent application Ser. No. 14/683,662 (U.S. Pat. No. 9,879,808) filed Apr. 10, 2015, which is a continuation of U.S. patent application Ser. No. 13/693,720 (U.S. Pat. No. 9,027,968) filed Dec. 4, 2012, which is a continuation of U.S. patent application Ser. No. 12/724,125 (U.S. Pat. No. 8,491,016) filed Mar. 15, 2010, which claims the benefit of U.S. Patent Application Ser. No. 61/160,603 filed on Mar. 16, 2009, the entireties of which are hereby incorporated by reference.

BACKGROUND

Aseptic coupling devices can be used to connect two or more sterilized pathways. For example, aseptic coupling devices can be used to couple a fluid pathway from a first piece of processing equipment or container to a fluid pathway from a second piece of processing equipment or container to establish a sterile pathway for fluid transfer therebetween.

Typical aseptic coupling devices require a "dry-to-dry" or "dry connection" that is created using one or more pathway clamping devices placed upstream of the aseptic coupling devices so that the aseptic coupling devices are kept free of fluid while the connection between the aseptic coupling devices is made. Once the sterile connection between the aseptic coupling devices is made, the clamping devices are removed to allow fluid to flow through the aseptic coupling devices.

SUMMARY

According to one aspect, an aseptic coupling device includes an inner member defining a fluid passage therethrough, a seal member coupled to a front surface of the inner member, a membrane coupled to the front surface of the inner member to cover the seal member, and a locking ring positioned to rotate about the inner member. The inner member is sized to be received in a member of another aseptic coupling device to form a pre-coupled state. When the membrane is removed, the seal member engages a second seal member of the other aseptic coupling device, and, upon turning of the locking ring, the seal member and the second seal member are compressed to form a coupled state in which a sterile flow path is created between the aseptic device and the other aseptic device.

According to another aspect, an aseptic coupling device includes a main body defining a fluid passage therethrough, a front portion coupled to the main body, the front portion defining a plurality of channels therein, a seal member coupled to a front surface of the main body, a membrane coupled to the front surface of the main body to cover the seal member, and a slot defined in the main body sized to receive a clip. The front portion is sized to a receive portion of another aseptic coupling device so that the clip engages the other aseptic coupling device to form a pre-coupled state. When the membrane is removed, the seal member engages a second seal member of the other aseptic device, and, upon turning of a locking ring on the other aseptic coupling device, barbs of the locking ring are received within the channels of the front portion to compress the seal member with the second seal member to form a coupled state in which a sterile flow path is created between the aseptic coupling device and the other aseptic coupling device.

In yet another aspect, a method for forming a sterile connection includes: inserting a first aseptic coupling device into a second aseptic coupling device; removing a first membrane from the first aseptic coupling device and a second membrane from the second aseptic coupling device; and rotating a locking clip on the first aseptic coupling device to compress a first seal member of the first aseptic coupling device with a second seal member of the second aseptic coupling device to form a sterile fluid passageway.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

FIG. 24 is a side view of the aseptic coupling arrangement of FIG. 23.

DETAILED DESCRIPTION

Figure 1:
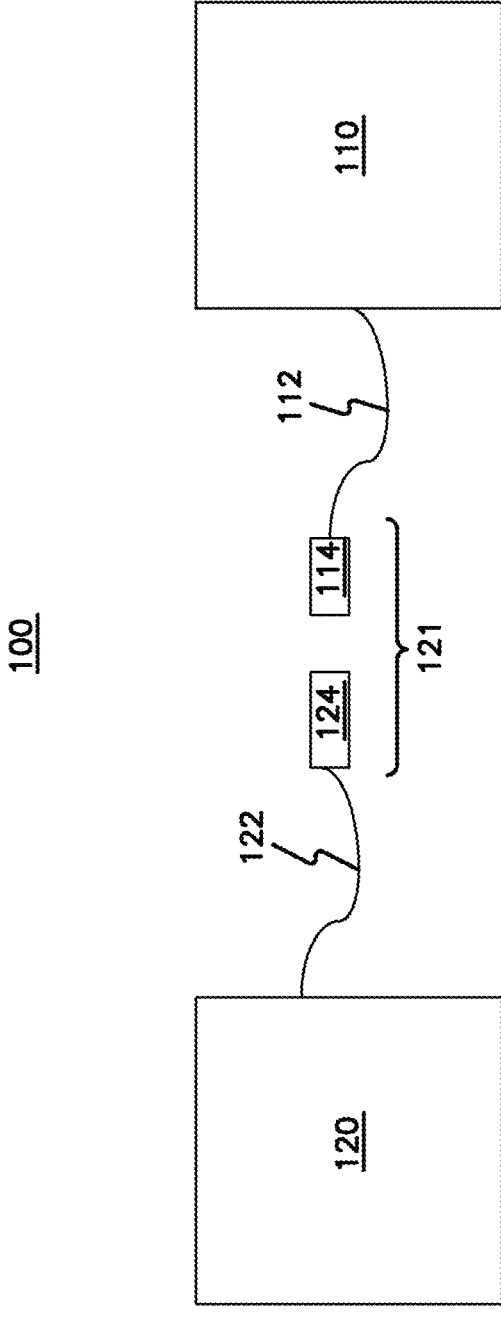
FIG. 1 is a schematic view of an example system including first and second pieces of processing equipment and an aseptic coupling device forming a sterile connection therebetween.
Figure 2:
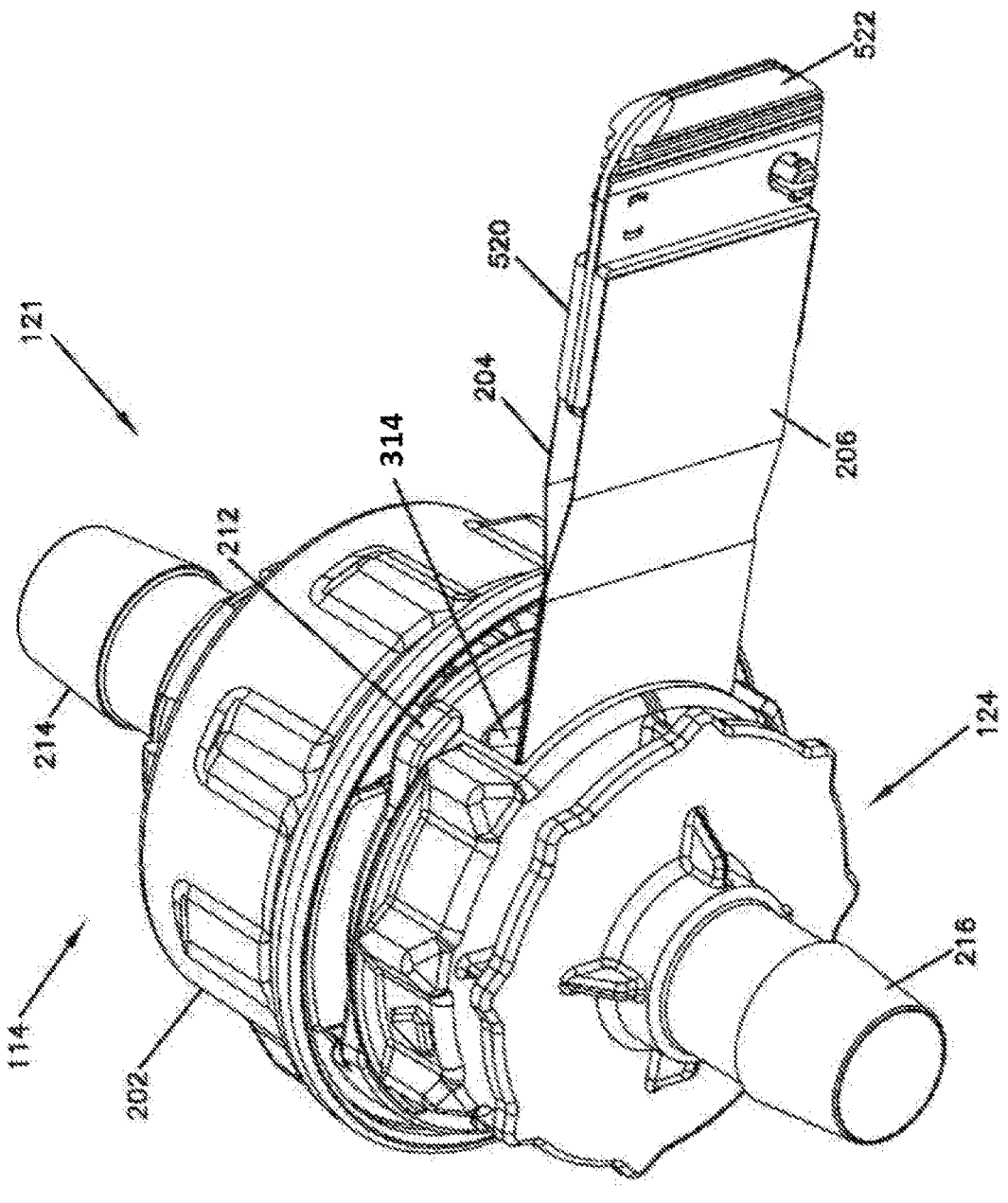
FIG. 2 is a perspective view of an example aseptic coupling arrangement in a pre-coupled state.
Figure 3:
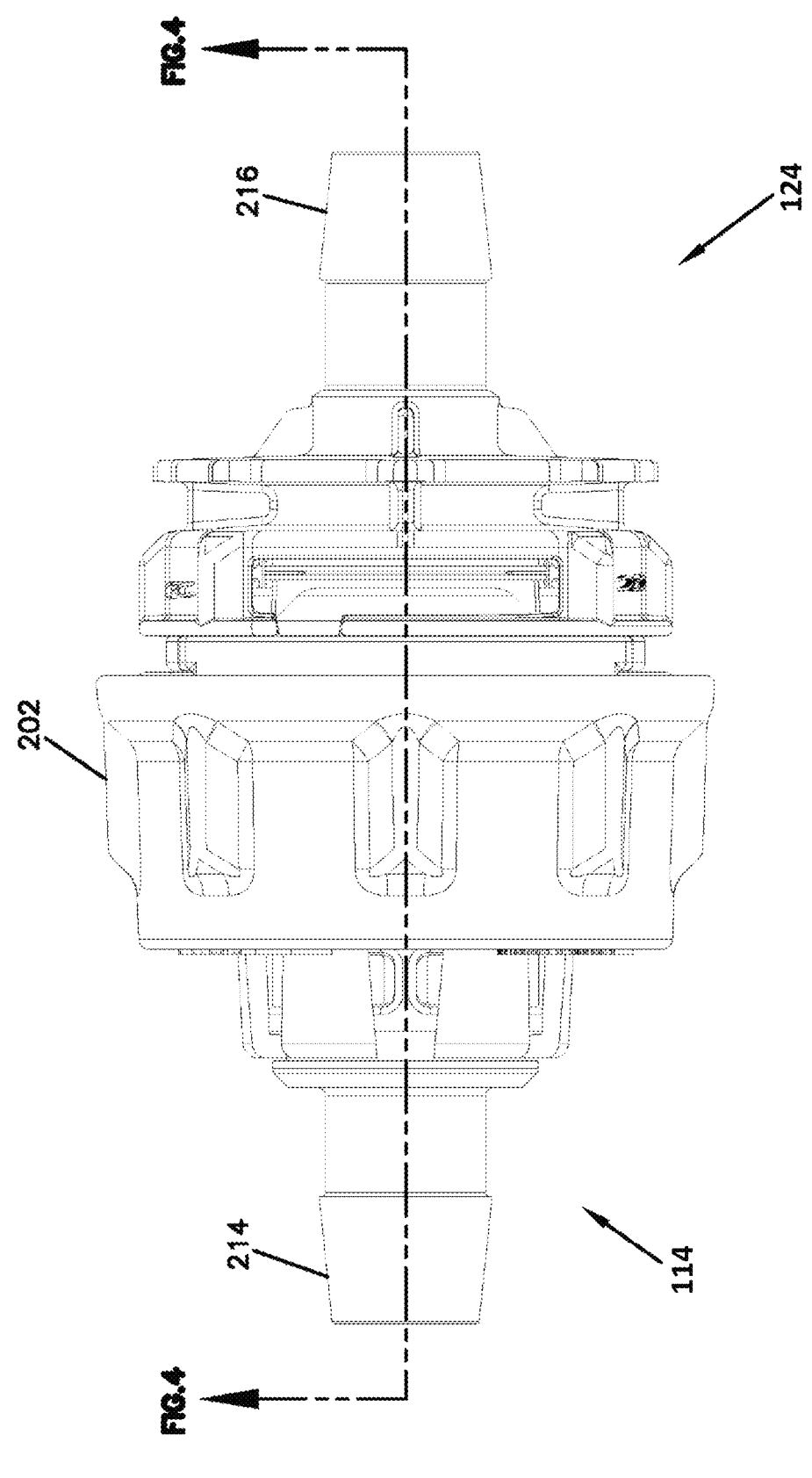
FIG. 3 is a top view of the aseptic coupling arrangement of FIG. 2.
Figure 4:
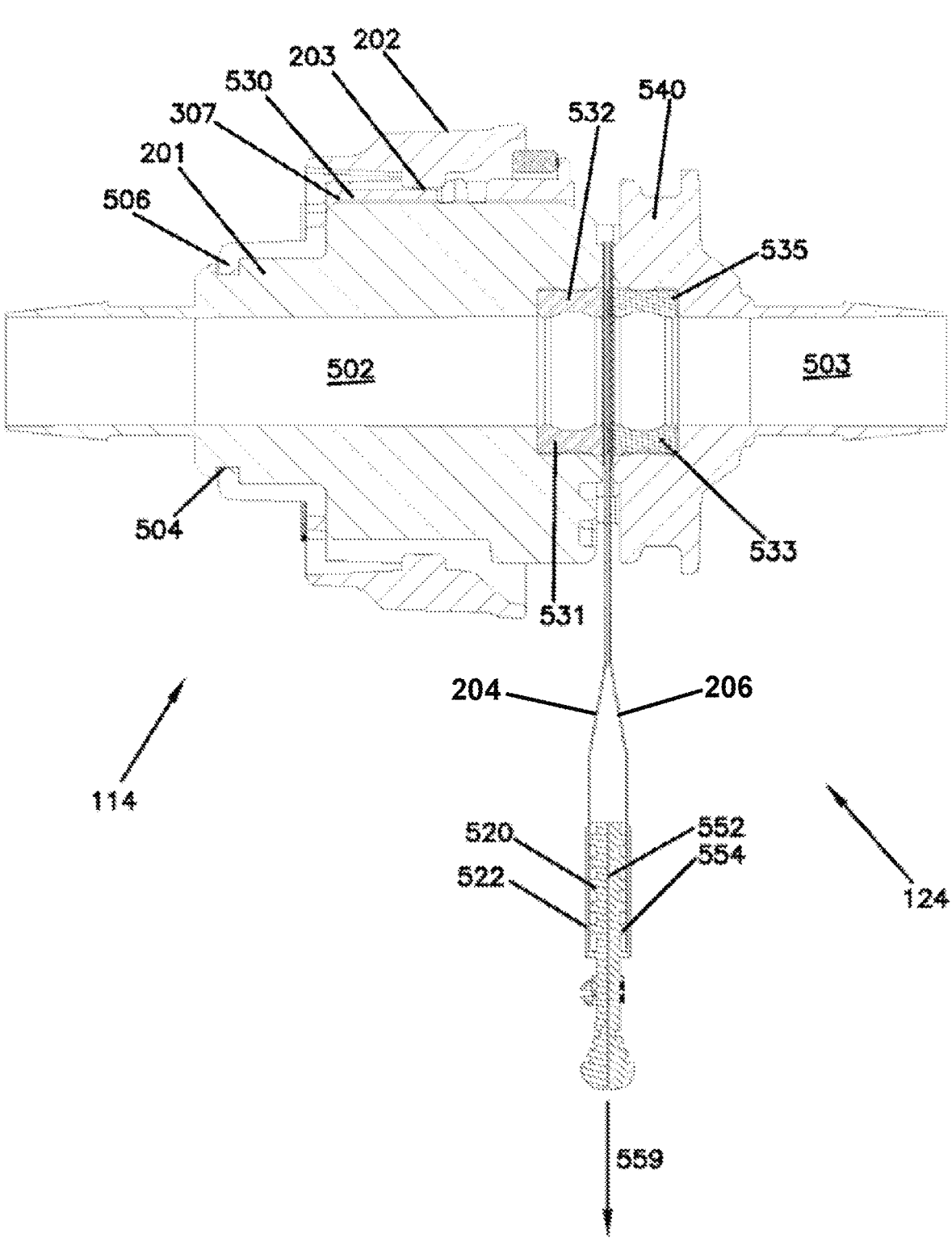
FIG. 4 is a cross-sectional view of the aseptic coupling arrangement of FIG. 3.
Figure 5:
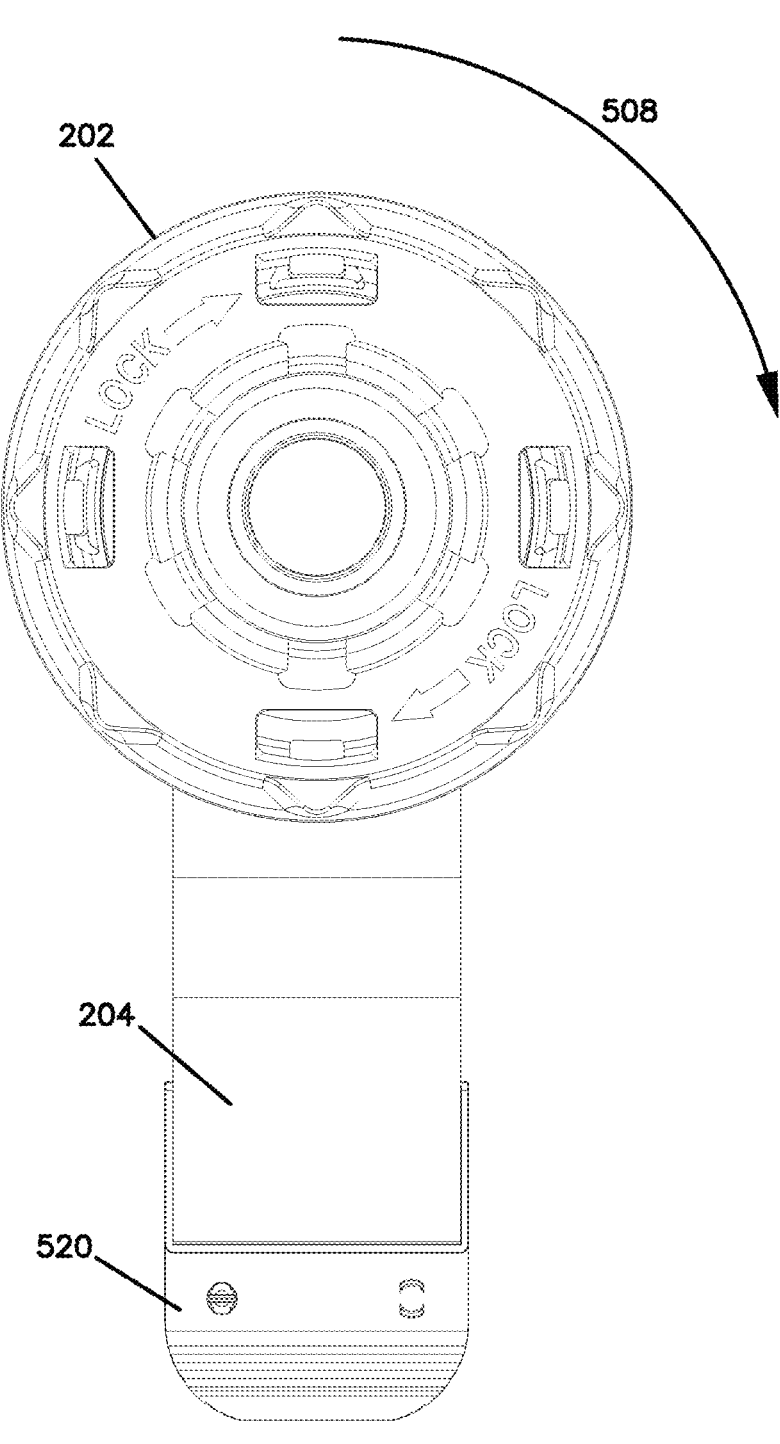
FIG. 5 is an end view of the aseptic coupling arrangement of FIG. 2.
Figure 6:
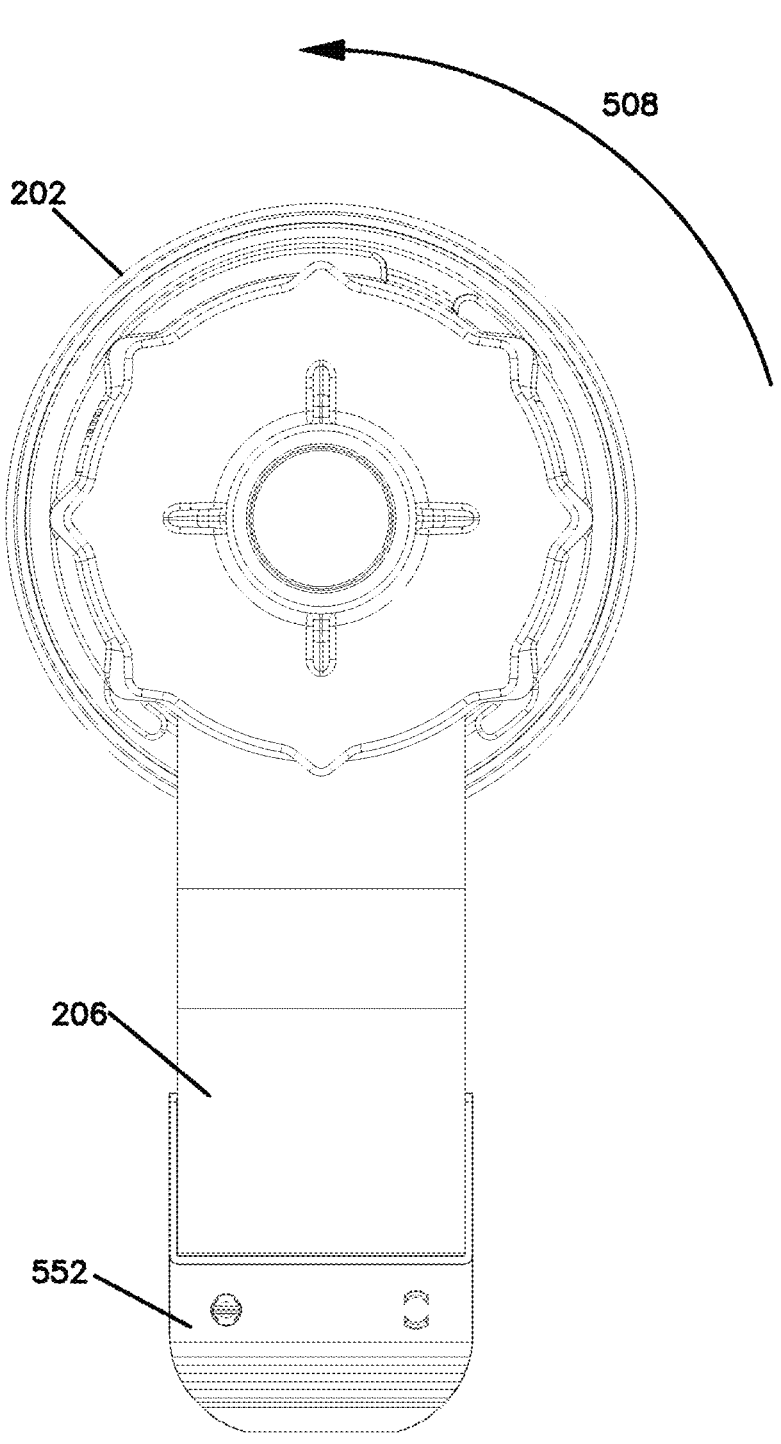
FIG. 6 is another end view of the aseptic coupling arrangement of FIG. 2.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "aseptic" refers to any process that maintains a sterilized surface or volume.

As used herein, the term "fluid" means any substance that can be made to flow including, but is not limited to, liquids, gases, granular or powdered solids, mixtures or emulsions of two or more fluids, suspensions of solids within liquids or gases, etc.

Referring now to FIG. 1, an example system 100 is shown. System 100 includes a first piece of processing equipment 110 and a second piece of processing equipment 120. In example embodiments, equipment 110 and 120 are bioreactors including biomaterial. In other embodiments, equipment 110 and 120 can be other apparatuses that require a sterile connection therebetween such as, for example, a bioreactor and a media bag or other receptacle.

Equipment 110 includes a fluid pathway 112 extending therefrom that is terminated by an aseptic coupling arrangement 121 including a first aseptic coupling device 114. Likewise, equipment 120 includes a fluid pathway 122 extending therefrom that is terminated by a second aseptic coupling device 124 of the aseptic coupling arrangement 121. In example embodiments, the environment within pathways 112 and 122 and aseptic coupling devices 114 and 124 are sterile.

Aseptic coupling device 114 can be connected to aseptic coupling device 124. Once aseptic coupling device 114 is connected to aseptic coupling device 124, a sterile fluid pathway is established between equipment 110 and equipment 120. Once the sterile fluid pathway is established, fluid can be transferred from equipment 110 to equipment 120, or vice versa.

Referring now to FIGS. 2-6, aseptic coupling devices 114 and 124 are shown in a pre-coupled state. In this state, the aseptic coupling devices 114, 124 are connected to one another. However, a sterile flow path has not yet been created because membranes associated with the aseptic coupling devices 114, 124 have not yet been removed.

In the example shown, aseptic coupling device 114 is a male coupling device, and aseptic coupling device 124 is a female coupling device. In the example shown, the devices 114, 124 are keyed so that the devices 114, 124 can only be coupled in one manner, as described below. In alternative embodiments, other configurations are possible.

In the example shown, the male aseptic coupling device 114 includes an inner member 201, a locking ring 202, and a membrane 204. See FIGS. 9-13.

Inner member 201 defines a fluid passage 502 through aseptic coupling device 114. Inner member 201 is coupled to a portion 214. In the example shown, portion 214 is barbed so that portion 214 can be connected to a fluid pathway (e.g., 112) such as a hose. Inner member 201 also includes a circular channel 504 that is formed to allow inner member 201 to be rotatably coupled to locking ring 202, as described below.

Figure 18:
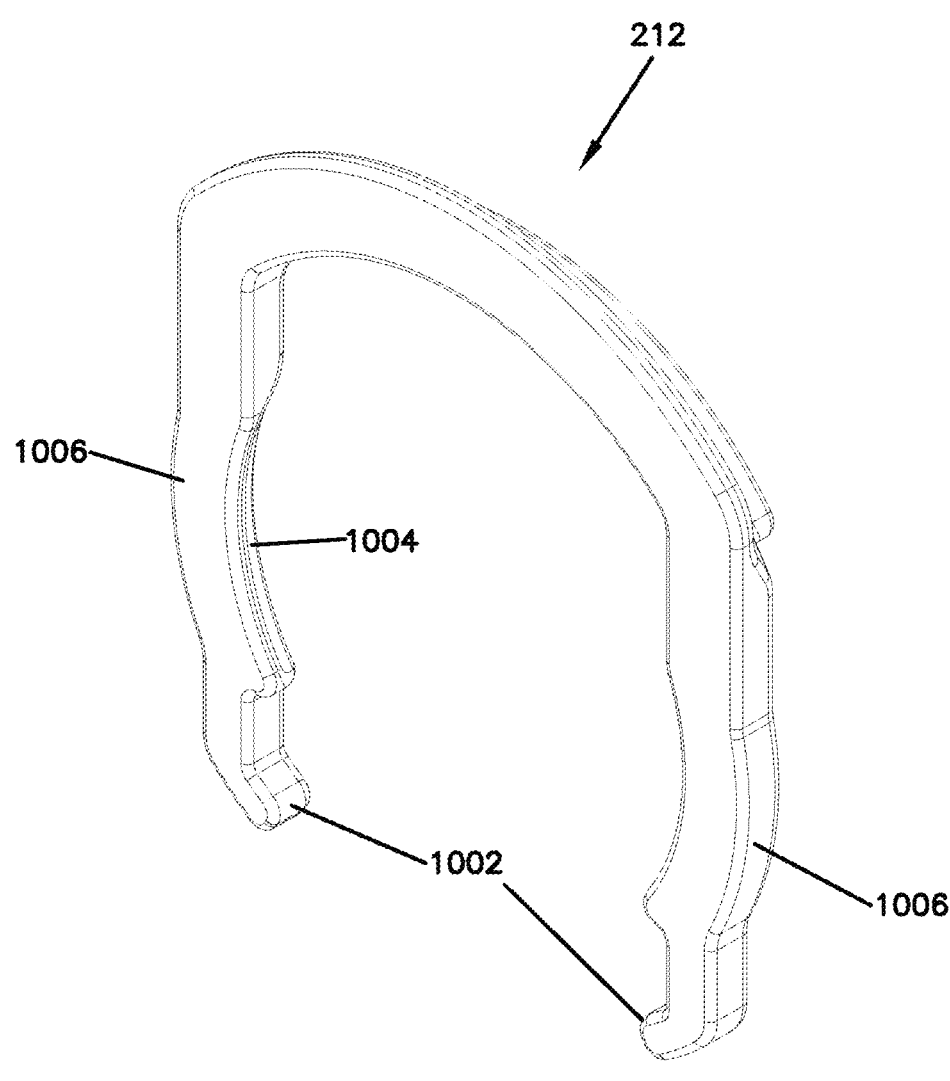
FIG. 18 is a perspective view of an example clip.

Inner member 201 also defines a channel 304. See FIGS. 8-10. Channel 304 is sized to receive a clip 212 (see FIG. 18) that is used to couple aseptic coupling device 114 to aseptic coupling device 124.

Figure 9:
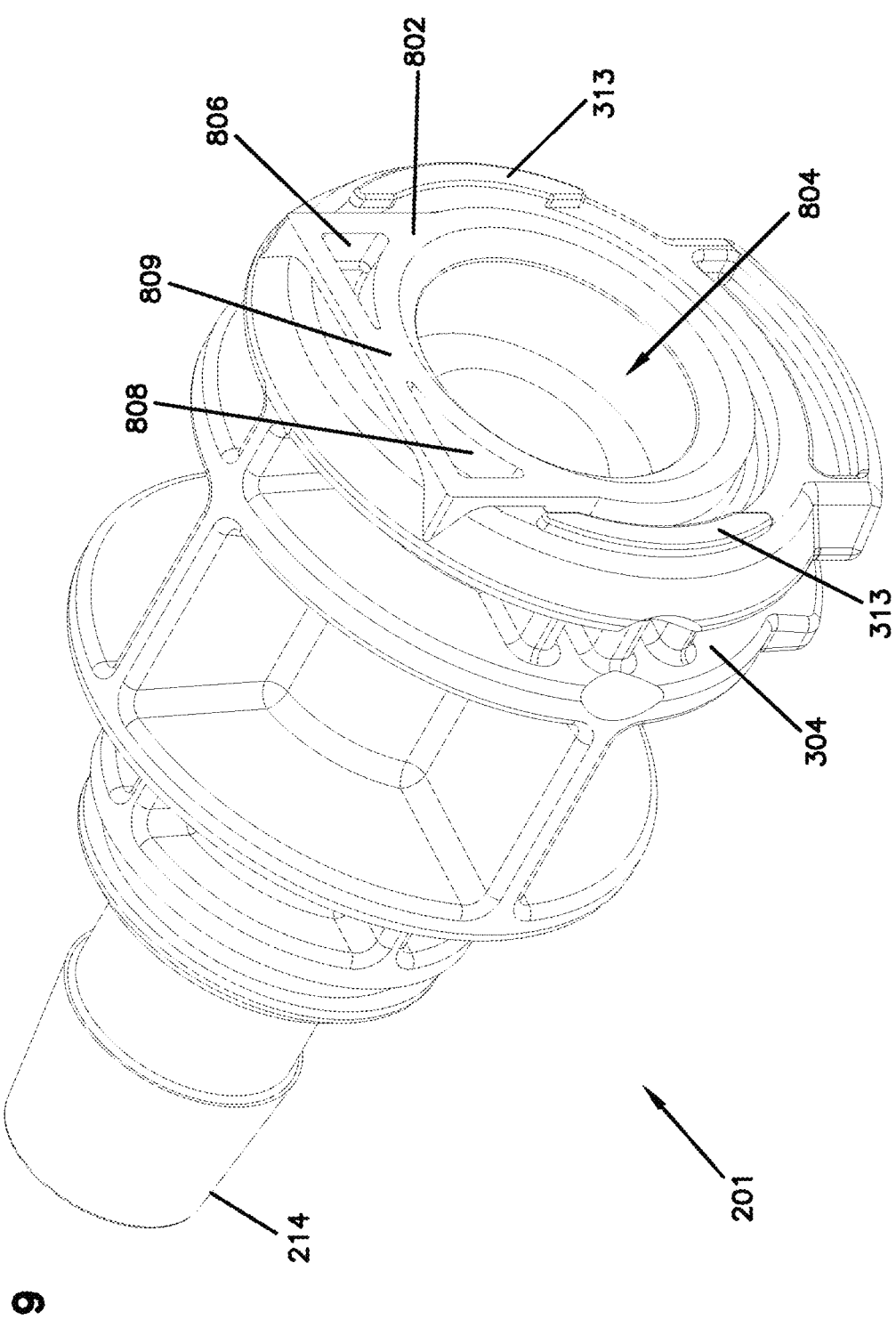
FIG. 9 is a perspective view of an inner member of the male aseptic coupling of FIG. 2.

Membrane 204 is coupled, using, for example, an adhesive, to a front surface 802 of inner member 201. As shown in FIG. 9, in example embodiments, front surface 802 includes an opening 804. Opening 804 allows fluid flow through inner member 201. Front surface 802 forms a generally "D" shape and surrounds the opening 804. An upper portion 809 of the front surface 802 allows membrane 204 to extend beyond opening 804 so that as membrane 204 is removed, the sterility of opening 804 is maintained even if membranes 204, 206 are pulled at different rates, as described below. Recess portions 806 and 808 are relief areas that minimize excessive pull forces.

Inner member 201 also has stops 313 formed adjacent front surface 802. As described further below, stops 313 engage complementary structures on the mating device to define a coupled position.

Figure 7:
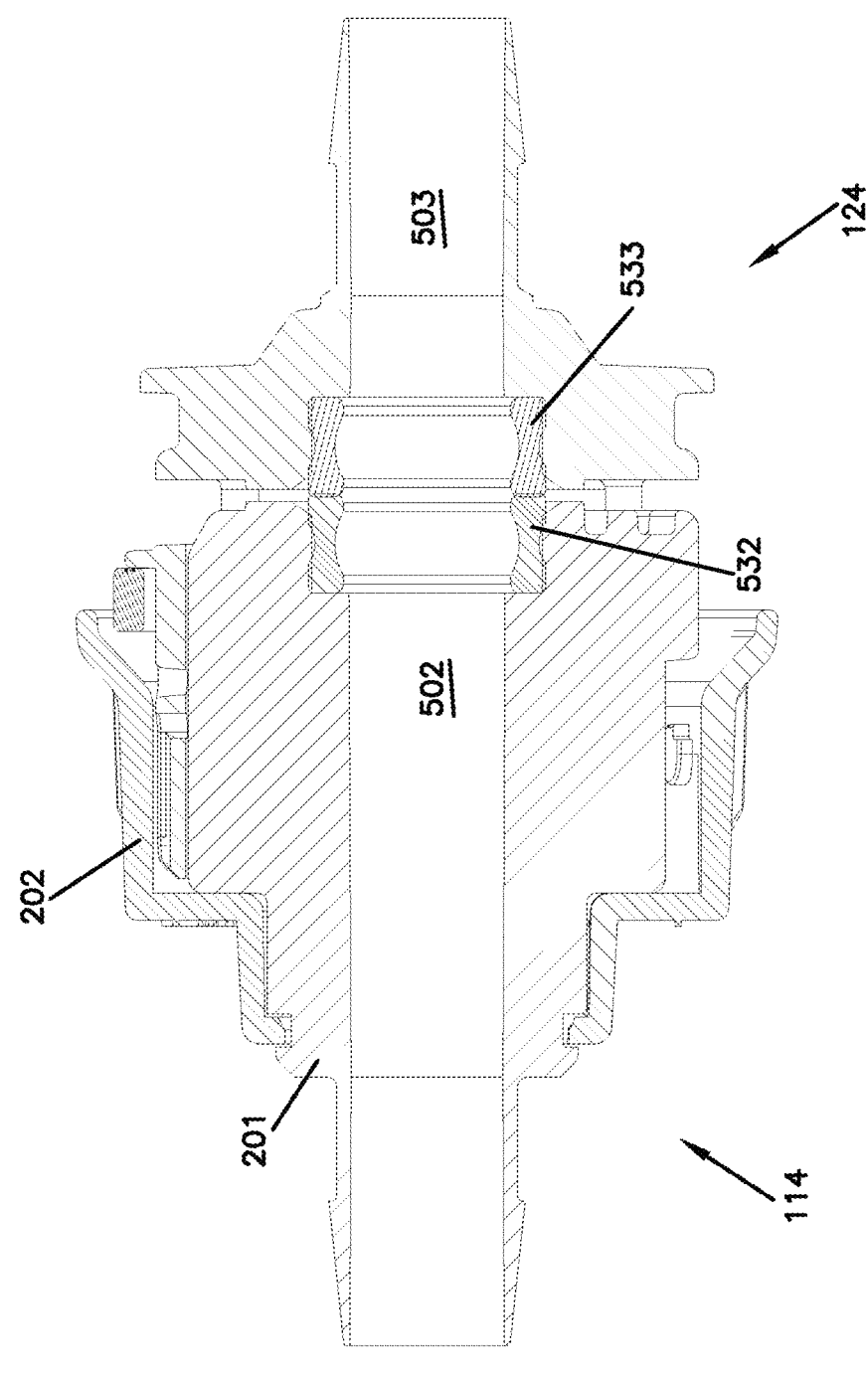
FIG. 7 is a cross-sectional view of the aseptic coupling arrangement of FIG. 2 in a coupled state.

In example embodiments, a seal member 532 is positioned in a window 531 formed by the inner member 201. Seal member 532 is positioned to engage a corresponding seal member 533 positioned in a window 535 on aseptic coupling device 124 when aseptic coupling devices 114, 124 are connected and membranes 204, 206 are removed, as described below. See FIG. 7.

As shown in FIGS. 2, 4, 5, 8, 16, and 17, membrane 204 extends through an opening 314 formed in the device 124. A handle portion 520 is coupled to an end 522 of membrane 204. In example embodiments, the handle portion 520 includes one or more attachment members 208, such as attachment members/apertures, that are positioned to engage attachment members 210 on a corresponding handle portion 552 coupled to the membrane 206 of the aseptic coupling device 124, as described further below.

Locking ring 202 includes a tab portion 506 that is positioned to be received in channel 504 formed by inner member 201. See FIGS. 4, 11, and 12. This allows locking ring 202 to be spun in a direction 508 (see FIG. 5) to lock aseptic coupling device 114 to aseptic coupling device 124, as described below. Knurls 507 formed on the locking ring 202 allow the user to easily grasp and rotate the locking ring 202.

Figure 8:
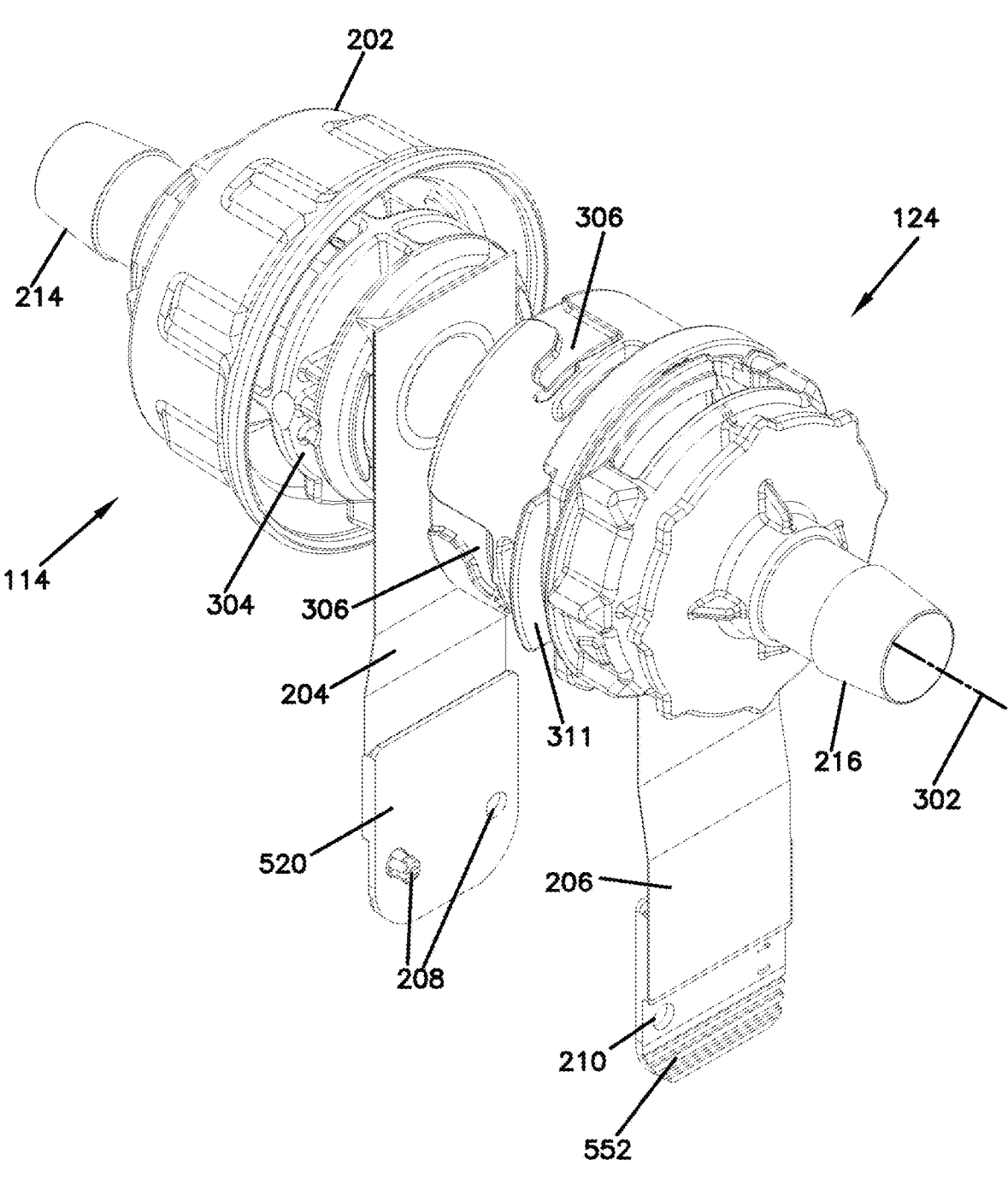
FIG. 8 is a perspective view of the aseptic coupling arrangement of FIG. 2 in an uncoupled state.
Figure 10:
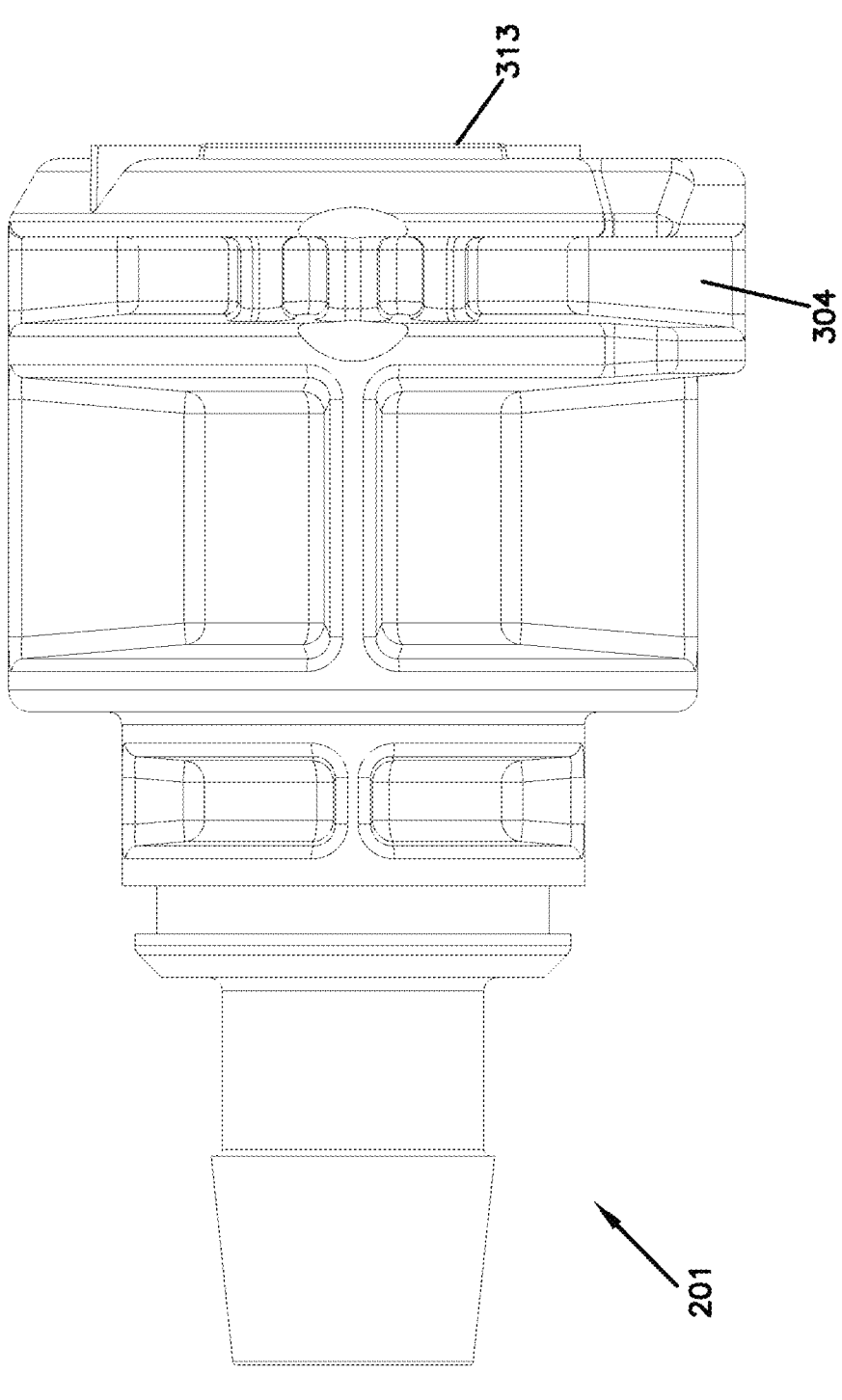
FIG. 10 is a side view of the inner member of the male aseptic coupling of FIG. 9.
Figure 11:
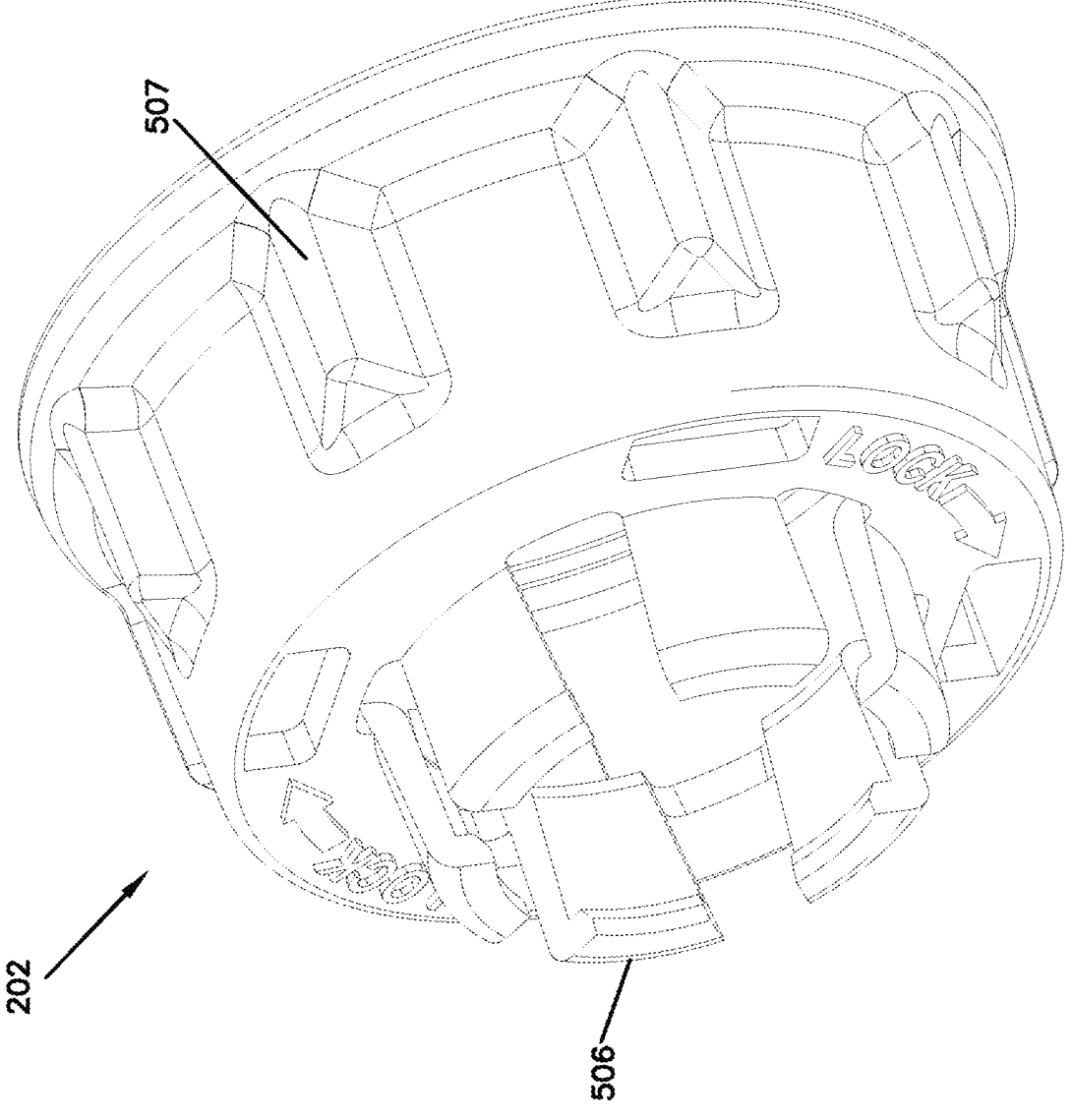
FIG. 11 is a perspective view of the locking ring of the male aseptic coupling of FIG. 2.
Figure 12:
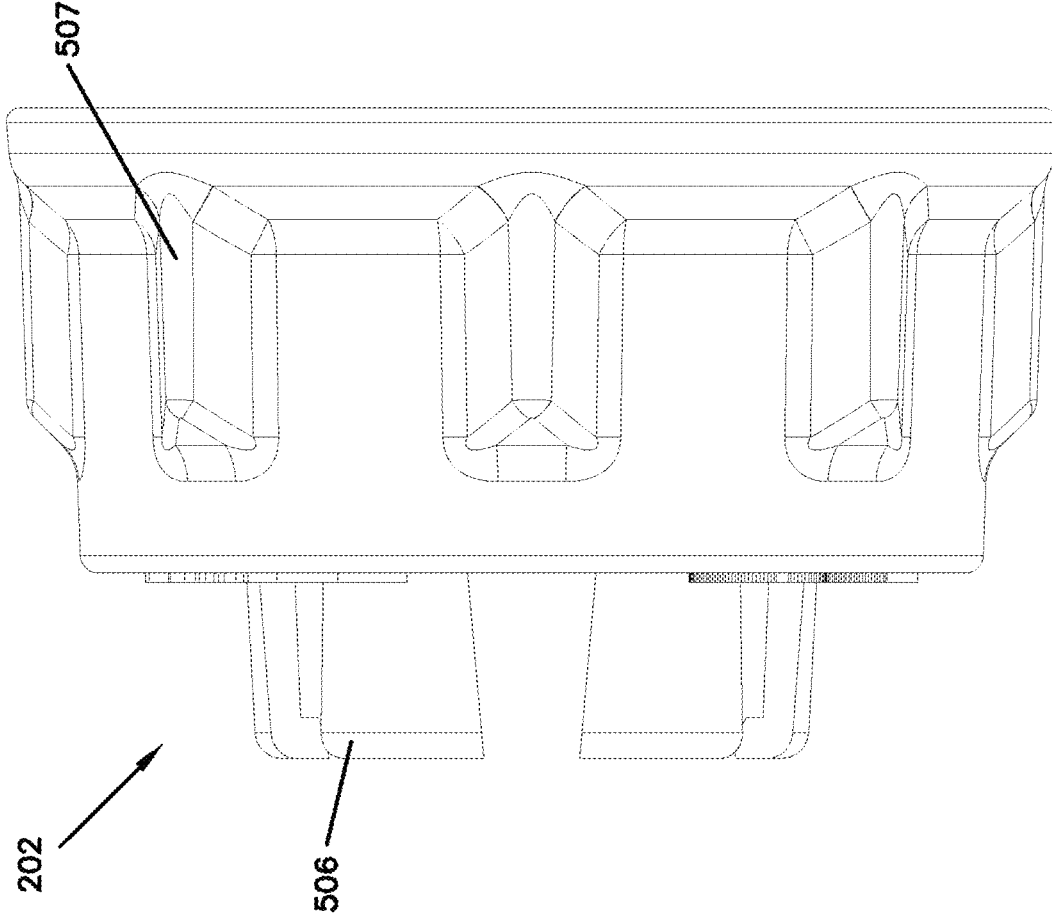
FIG. 12 is a side view of the locking ring of the male aseptic coupling of FIG. 11.
Figure 13:
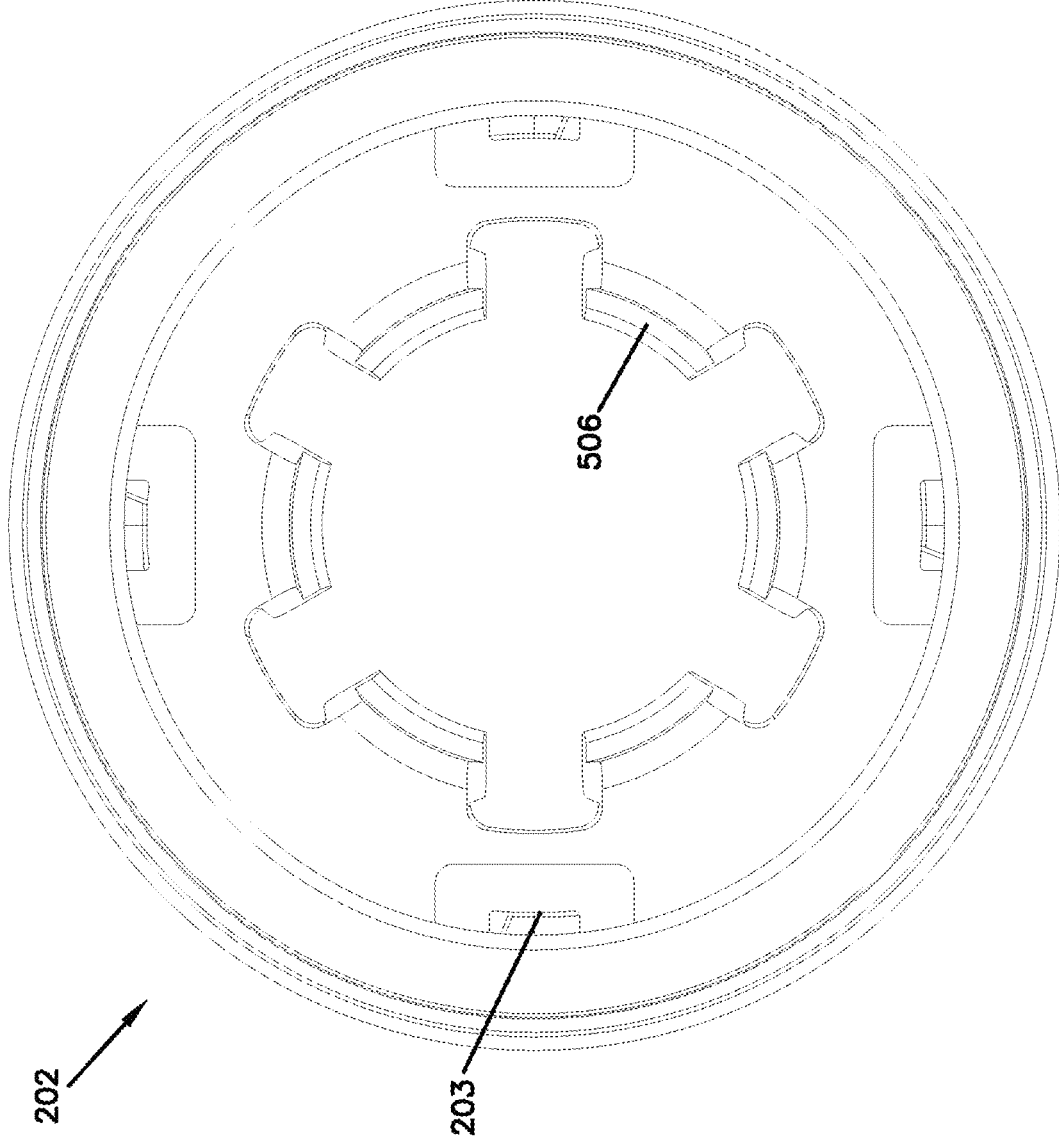
FIG. 13 is an end view of the locking ring of the male aseptic coupling of FIG. 11.

Locking ring 202 also includes barbs 203 (see FIGS. 4 and 13) extending from and spaced about an inner periphery of locking ring 202. As shown in FIGS. 8-10 and described further below, barbs 203 are received in corresponding channels 306 formed by aseptic coupling device 124 to couple aseptic coupling device 114 thereto. In one embodiment, four barbs 203 are spaced radially about the inner periphery of locking ring 202.

Aseptic coupling device 124 includes a front portion 530 configured to be coupled to aseptic coupling device 114, and a barbed portion 216 configured to be coupled to a fluid source. A fluid passage 503 is formed therethrough.

Front portion 530 includes channels 306 that extend from a front edge 307 of front portion 530. In the example show, each channel 306 includes an inlet portion 902 that extends generally axially, and a locking portion 904 that extends generally radially. The inlet portion 902 is sized to receive one barb 203 of locking ring 202 of aseptic coupling device 114. When the locking ring 202 is rotated in direction 508, barb 203 extends into and is captured by locking portion 904 of channel 306. In example embodiments, three channels 306 are spaced axially about front portion 530 to correspond to barbs 203 of locking ring 202.

Front portion 530 also defines slots 311 that are positioned to receive clip 212. Barbs 1002 on clip 212 engage a bottom surface 317 of device 124 (see FIG. 18). Ramped portions 1004 on each side arm 1006 of the clip 212 extend radially inward through slots 311 to engage channel 304 on aseptic coupling device 114. The ramped surfaces of the ramped portions 1004 allow the device to ride along the ramped portions 1004 and push arms 1006 away from one another to clear the ramped portions 1004. Upon clearance, the ramped portion 1004 move back into place within channel 304 to couple the devices 114, 124. In one example, the ramped portions 1004 make a "clicking" noise as they clear and enter the channel 304 to provide the user with audible and/or tactile feedback of a positive coupling.

Membrane 206 is coupled to a front surface 910 of aseptic coupling device 124. See FIG. 17. In examples, surface 910 is generally "D" shaped and surrounds opening 908. Similar to front surface 802, an upper portion 909 of front surface 910 allows membrane 206 to extend beyond opening 908 so that as membrane 206 is removed, the sterility of opening 804 is maintained even if membranes 204, 206 are pulled at different rates, as described below.

Figure 33:
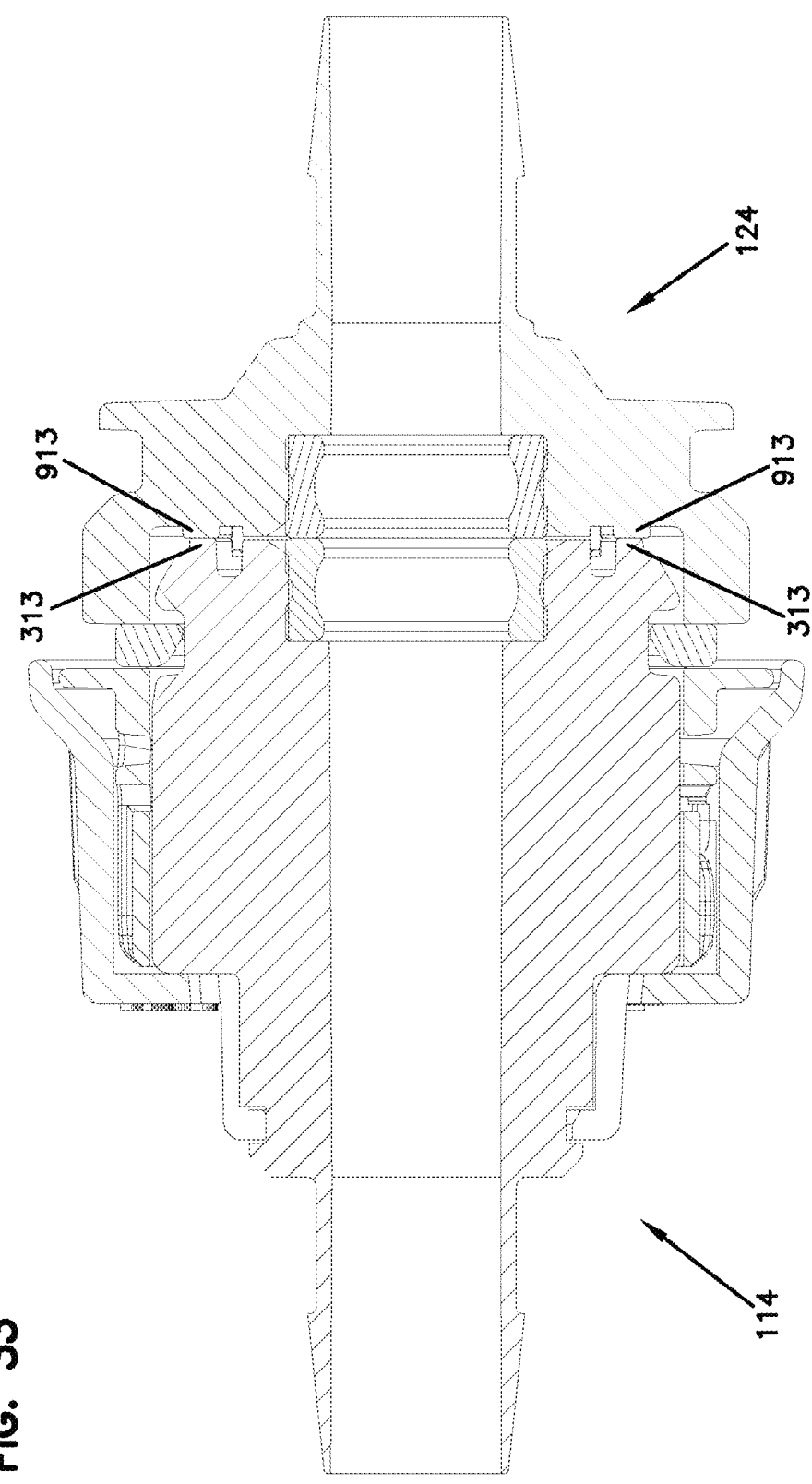
FIG. 33 is another cross-sectional view of the aseptic coupling arrangement of FIG. 2 in a coupled state.

Adjacent front surface 910 are formed stops 913. The stops 913 engage stops 313 on the device 114 when the device is positioned in the coupled state. The stops 313, 813 define the closes position that the devices 114, 124 can come together. See FIG. 33. In this manner, the stops 313, 813 define the amount of compression in seals 532, 533 when the devices 114, 124 are in the coupled state. The stops 313, 913 thereby maintain the desired compression and minimize the possibility of side load leakage.

An end 554 of membrane 206 includes a handle portion 552 that includes attachment members 210 that are positioned to engage attachment members 208 on the corresponding membrane 206 of the aseptic coupling device 124, as described further below.

Figure 19:
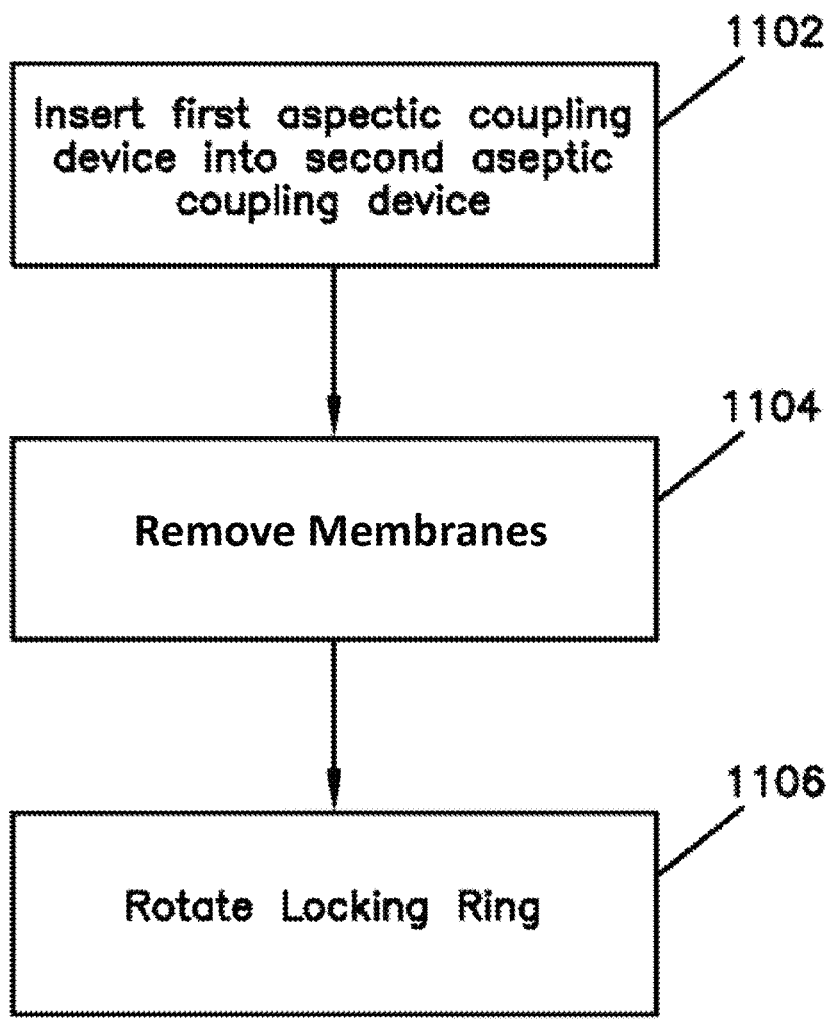
FIG. 19 is an example method for connecting the aseptic coupling device.

Referring now to FIG. 19, an example method 1100 for connecting aseptic coupling device 114 to aseptic coupling device 124 is shown.

Figure 14:
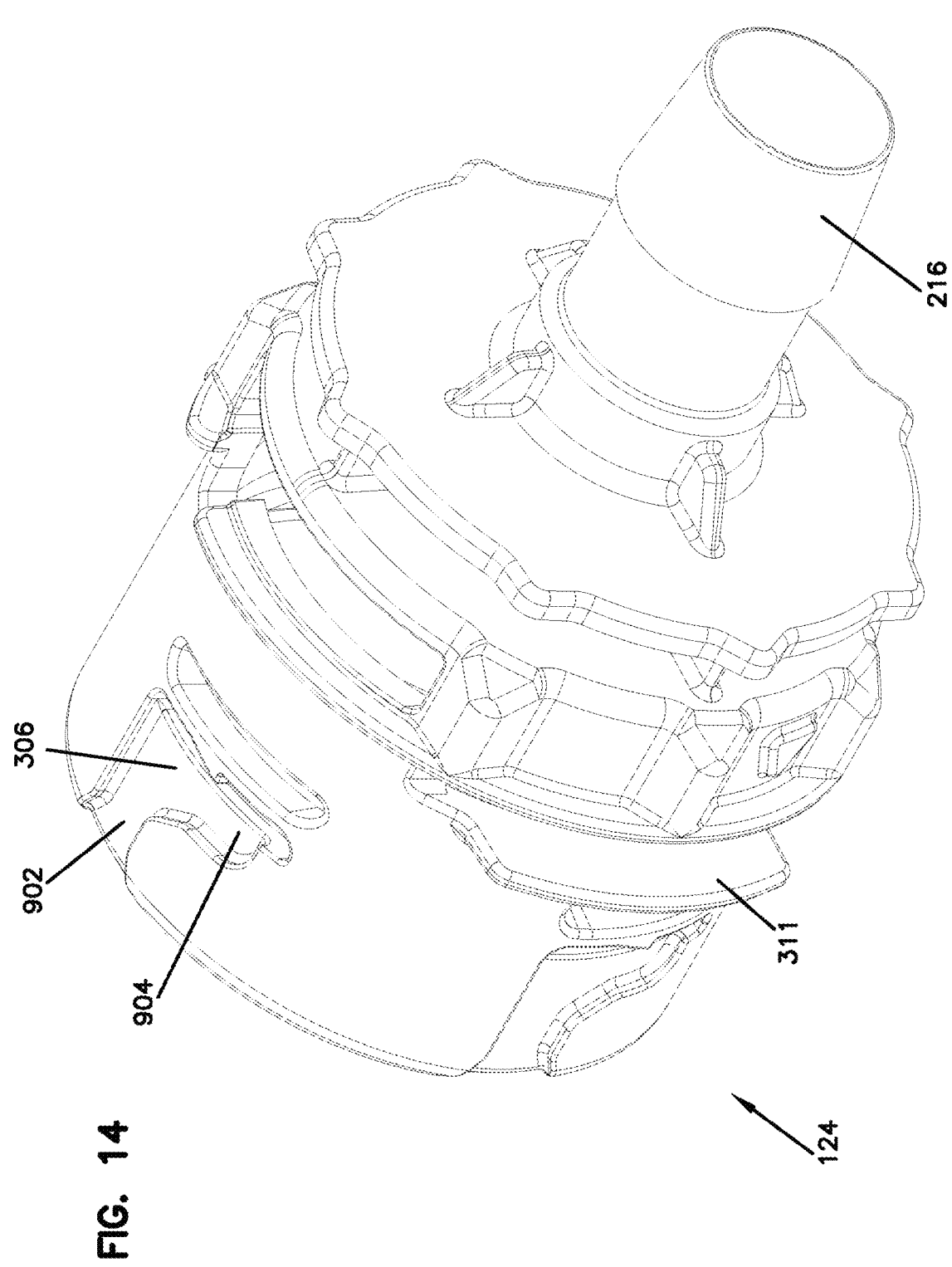
FIG. 14 is a perspective view of a female aseptic coupling of FIG. 2.
Figure 15:
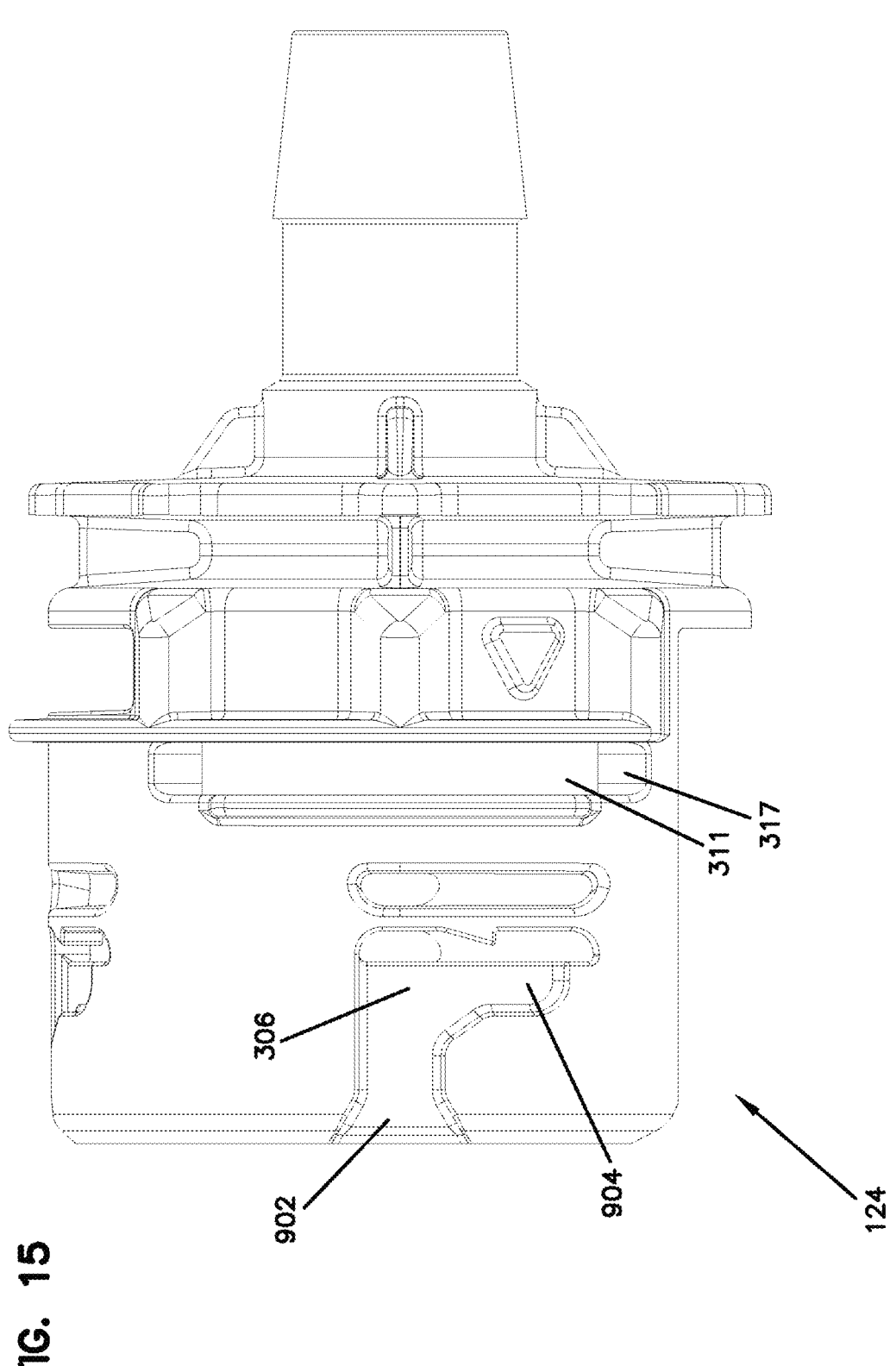
FIG. 15 is a side view of the female aseptic coupling of FIG. 14.
Figure 16:
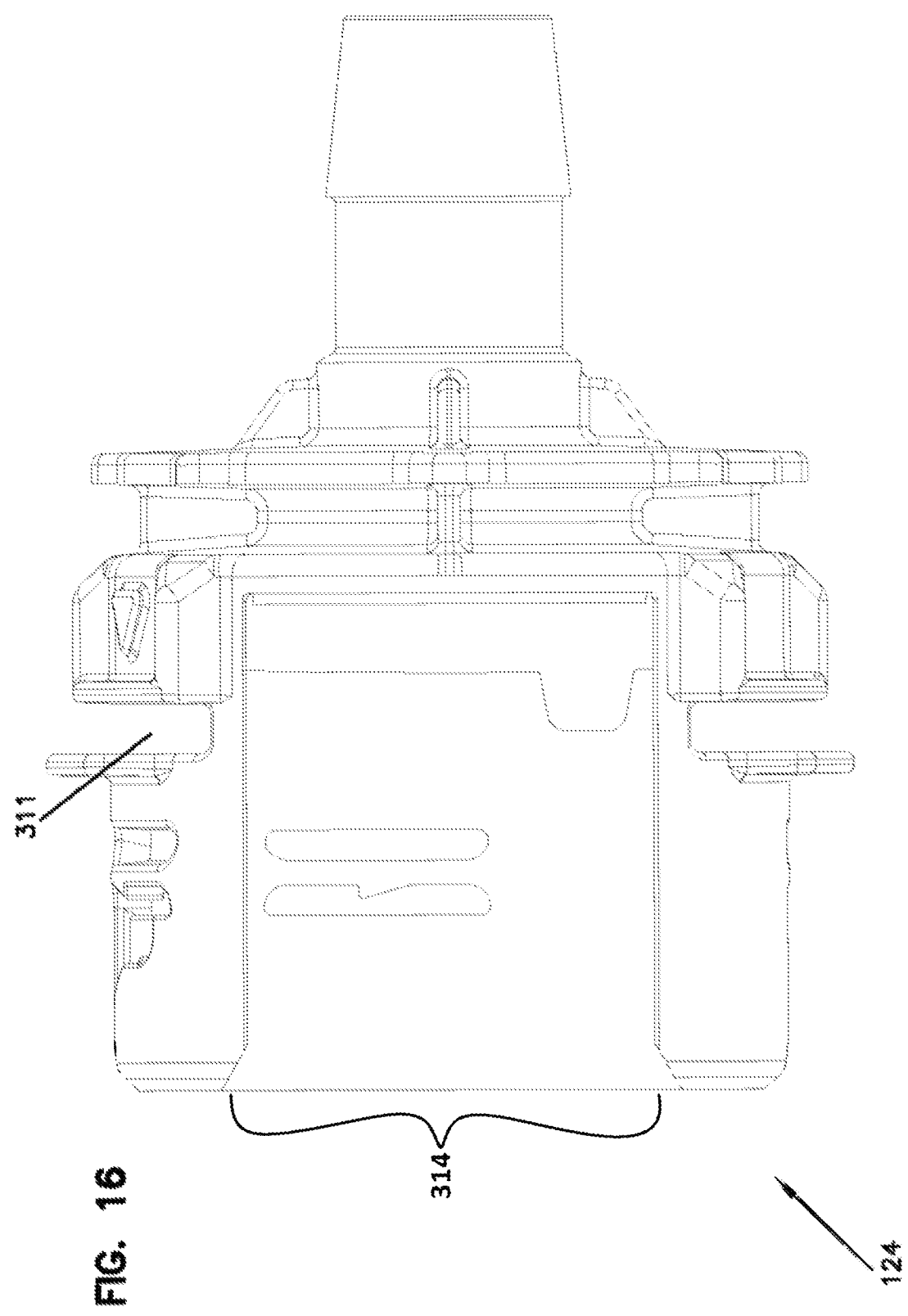
FIG. 16 is a bottom view of the female aseptic coupling of FIG. 14.
Figure 17:
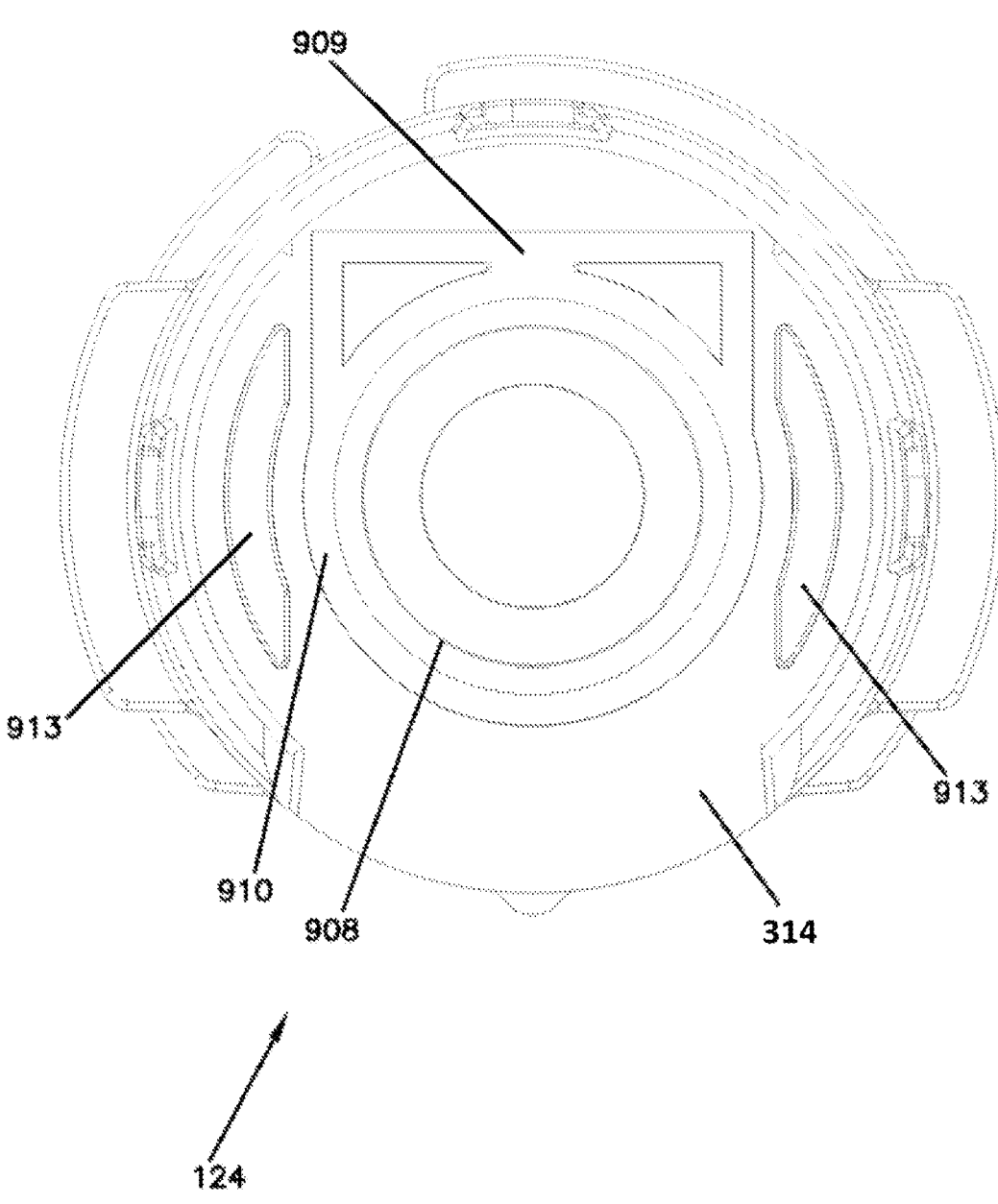
FIG. 17 is an end view of the female aseptic coupling of FIG. 14.

First, at operation 1102, front portion 530 of aseptic coupling device 114 is inserted into aseptic coupling device 124 along centerline 302. During insertion, the membrane 204 (while hanging downward as shown in FIG. 8) enters into the opening 314 to become adjacent to the membrane 206 (FIG. 2), and barbs 203 (FIG. 13) are received in inlet portions 902 (FIG. 14) of channels 306. In addition, front portion 530 surrounds inner member 201. When front portion 530 is fully inserted, barbs 1002 of clip 212 are received in channel 304 on aseptic coupling device 114. In this position (referred to as "pre-coupled"), aseptic coupling device 114 is coupled to aseptic coupling device 124.

Next, at operation 1104, the attachment members 210 on handle portion 552 of membrane 206 are connected to attachment members 208 on handle portion 520 of membrane 204. Once connected, handle portions 520, 552 are grasped, and a force in a direction 559 is applied. As membranes 204, 206 are pulled in direction 559, membranes 204, 206 roll in on one another and seals 532, 533 in ends 201 and 540 of each of aseptic coupling devices 114, 124 engage to form a sterile connection.

Once membranes 204, 206 are removed, locking ring 202 is rotated (stage 1106) in direction 508 so that barbs 203 enter locking portions 904 of channels 306. As barbs 203 move along locking portions 904, aseptic coupling device 114 is pulled slightly closer to aseptic coupling device 124 to compress the seal members 532, 533 together. At this position (referred to as "coupled"), an aseptic pathway exists through passages 502, 503 of the aseptic coupling devices 114, 124. See FIG. 7. As noted above, the stops 313, 913 define the level of compression for the seal members 532, 533. See FIG. 33.

Figure 20:
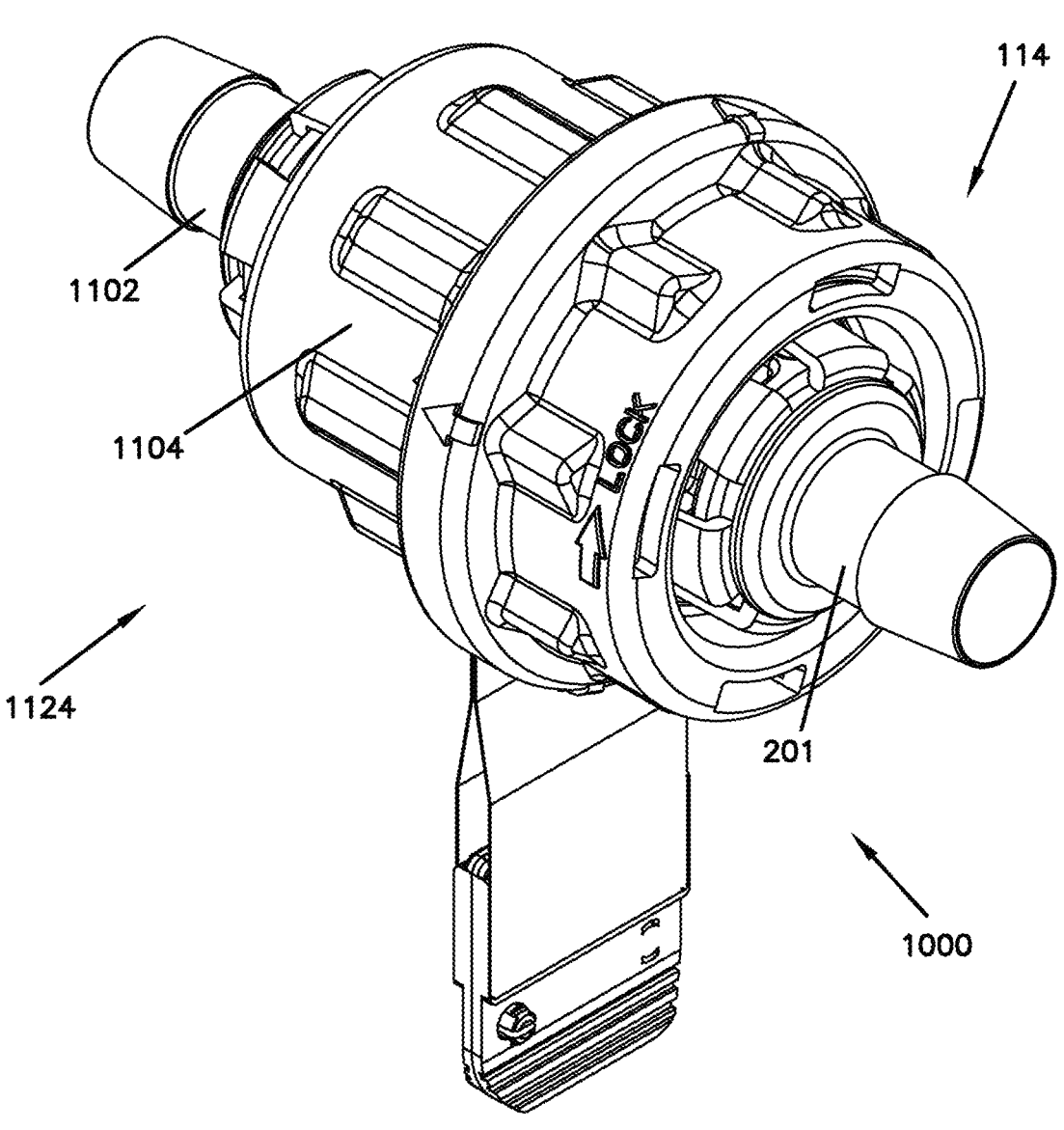
FIG. 20 is a first perspective view of another aseptic coupling arrangement in a pre-coupled state.
Figure 21:
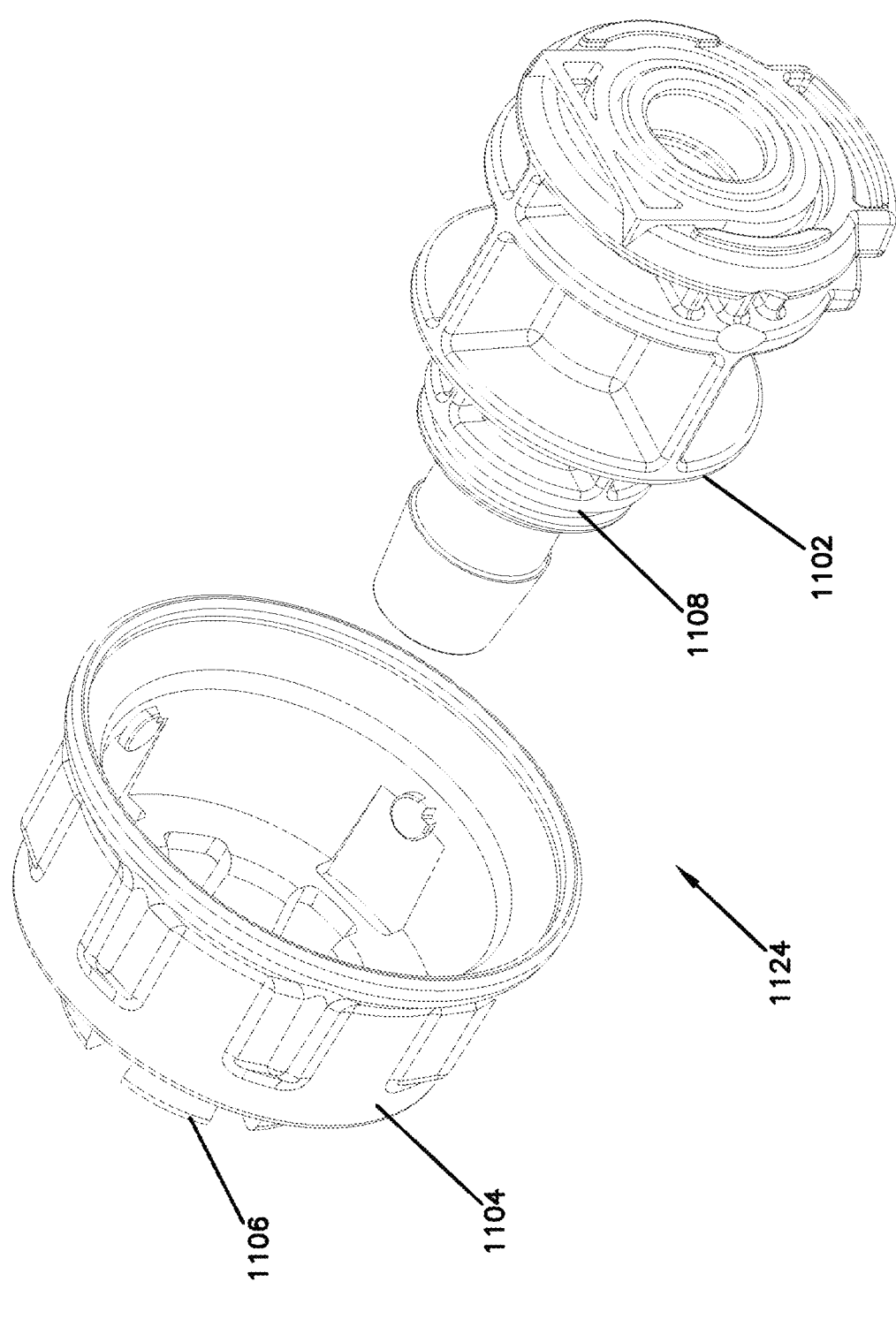
FIG. 21 is a first exploded perspective view of the male coupling device of the arrangement of FIG. 20.
Figure 22:
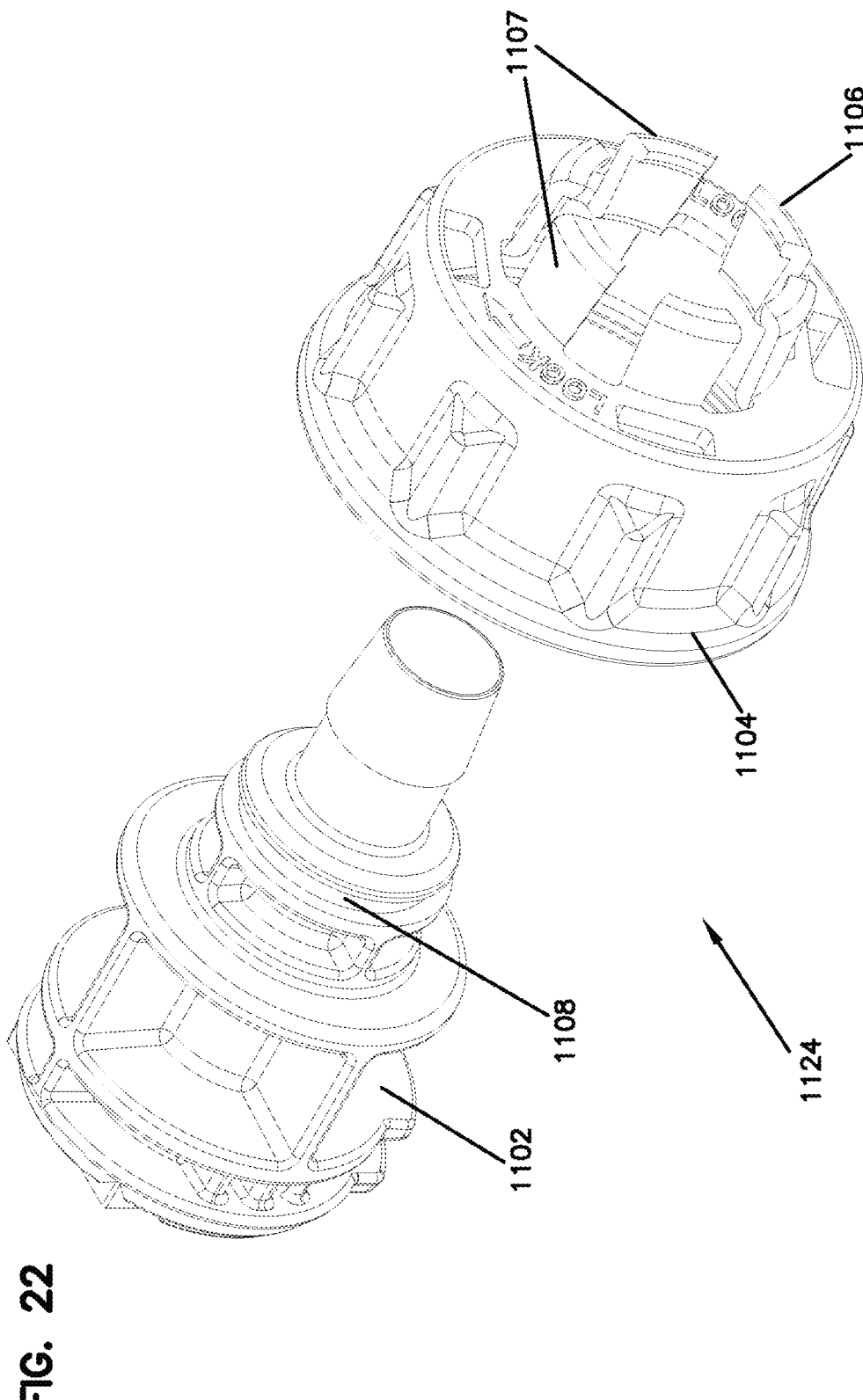
FIG. 22 is a second exploded perspective view of the male coupling device of the arrangement of FIG. 20.

Referring now to FIGS. 20-22, an alternative embodiment of an aseptic coupling arrangement 1000 is shown. In the example shown, aseptic coupling device 114 is identical to that described above, and an aseptic coupling device 1124 is a male coupling that is similar to aseptic coupling device 124 describe above.

However, aseptic coupling device 1124 includes a separate inner member 1102 and outer member 1104. Inner member 1102 is identical in shape to inner member 201 of aseptic coupling device 114. This allows both components to be molded using the same machinery.

Outer member 1104 includes a tab portion 1106 with a plurality of members 1107 that are positioned to be received in a channel 1108 formed by inner member 1102. This allows outer member 1104 to be coupled to inner member 1102 and spin relative thereto. Other configurations are possible.

Figure 23:
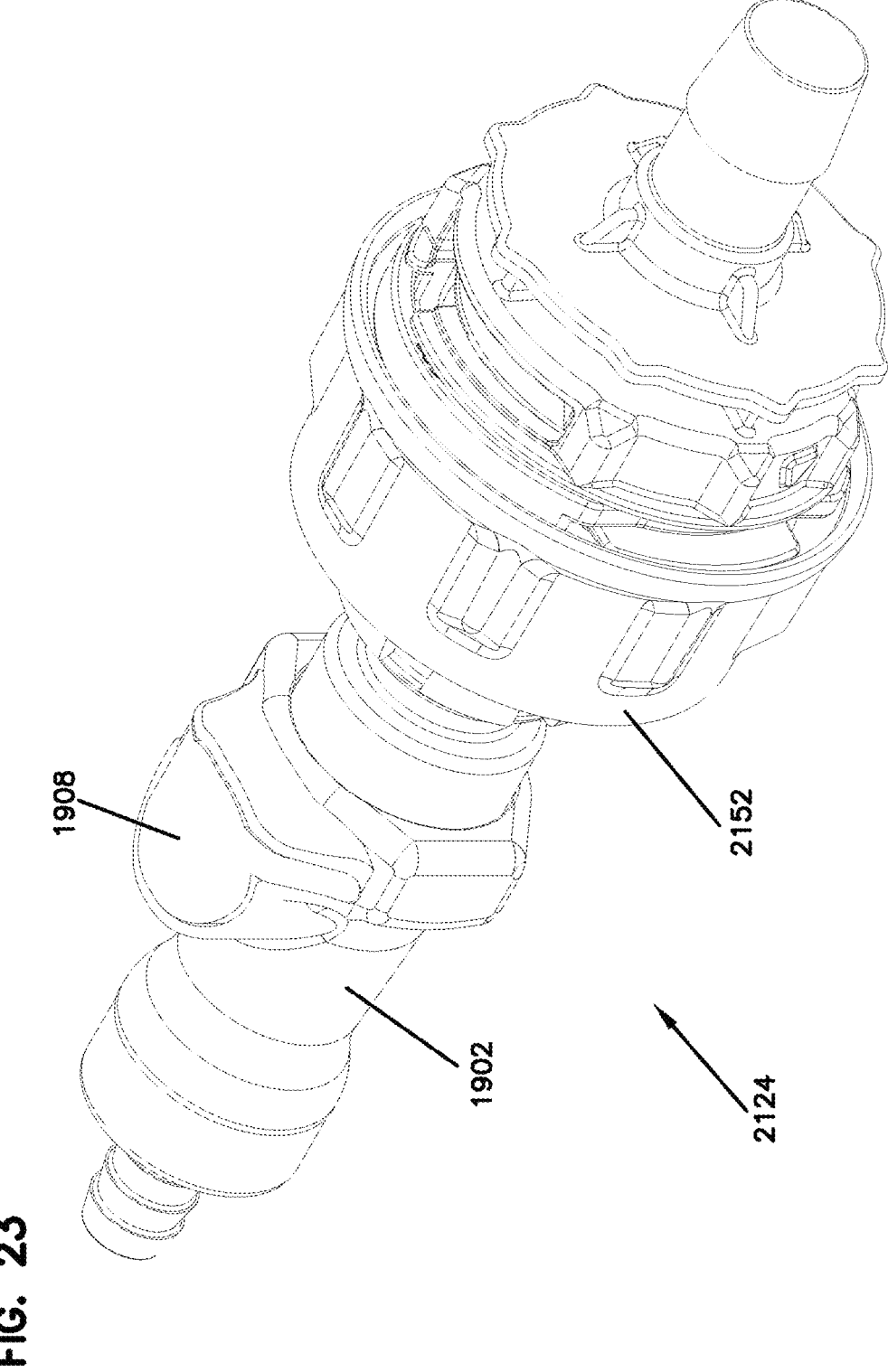
FIG. 23 is a perspective view of another aseptic coupling arrangement having a coupler attached thereto.
Figure 24:
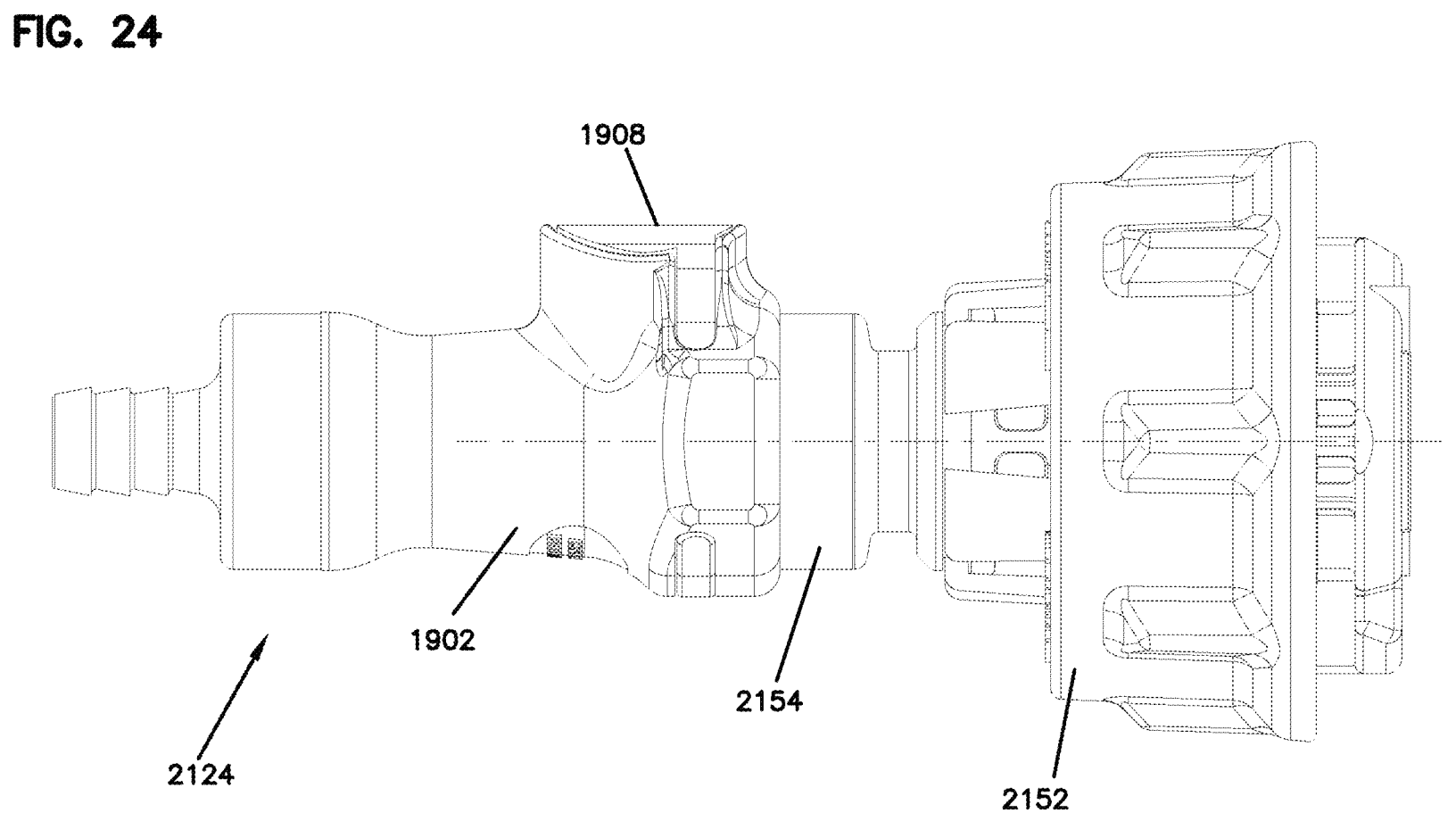
Figure 25:
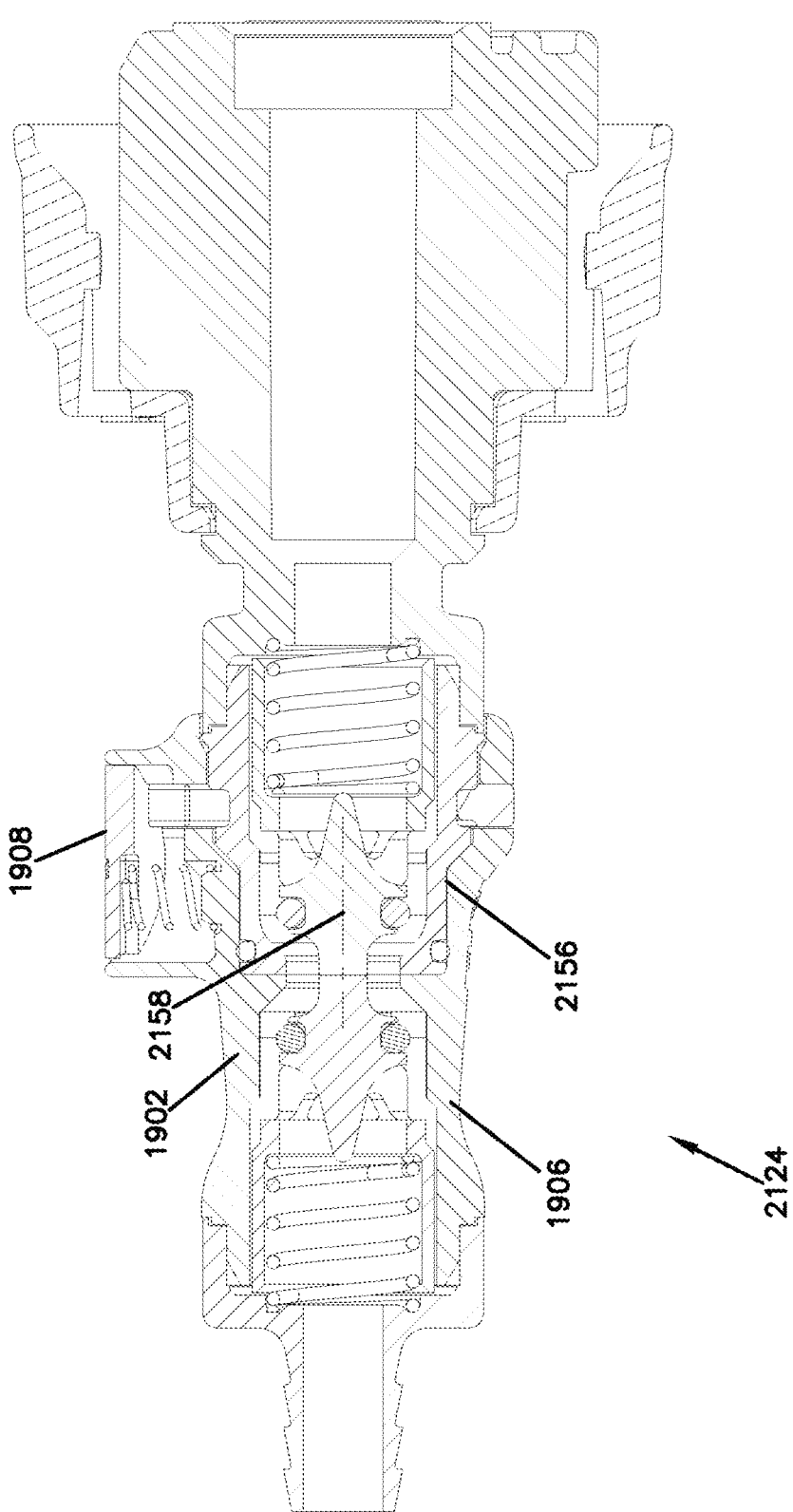
FIG. 25 is a cross-sectional view of the aseptic coupling arrangement of FIG. 23.
Figure 26:
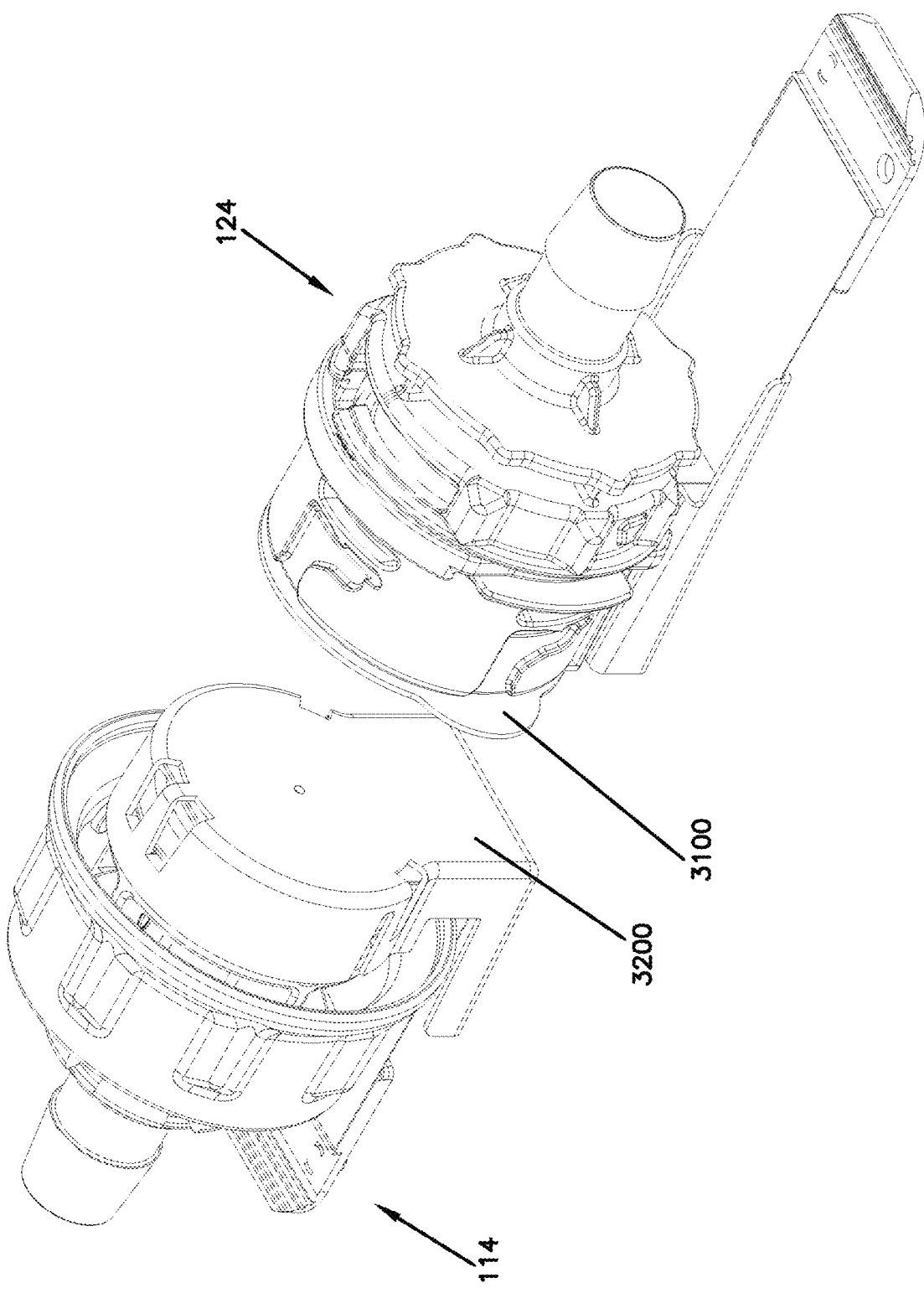
FIG. 26 is a first perspective view of the male and female aseptic coupling devices of FIG. 2 in an uncoupled state and with caps attached thereto.
Figure 27:
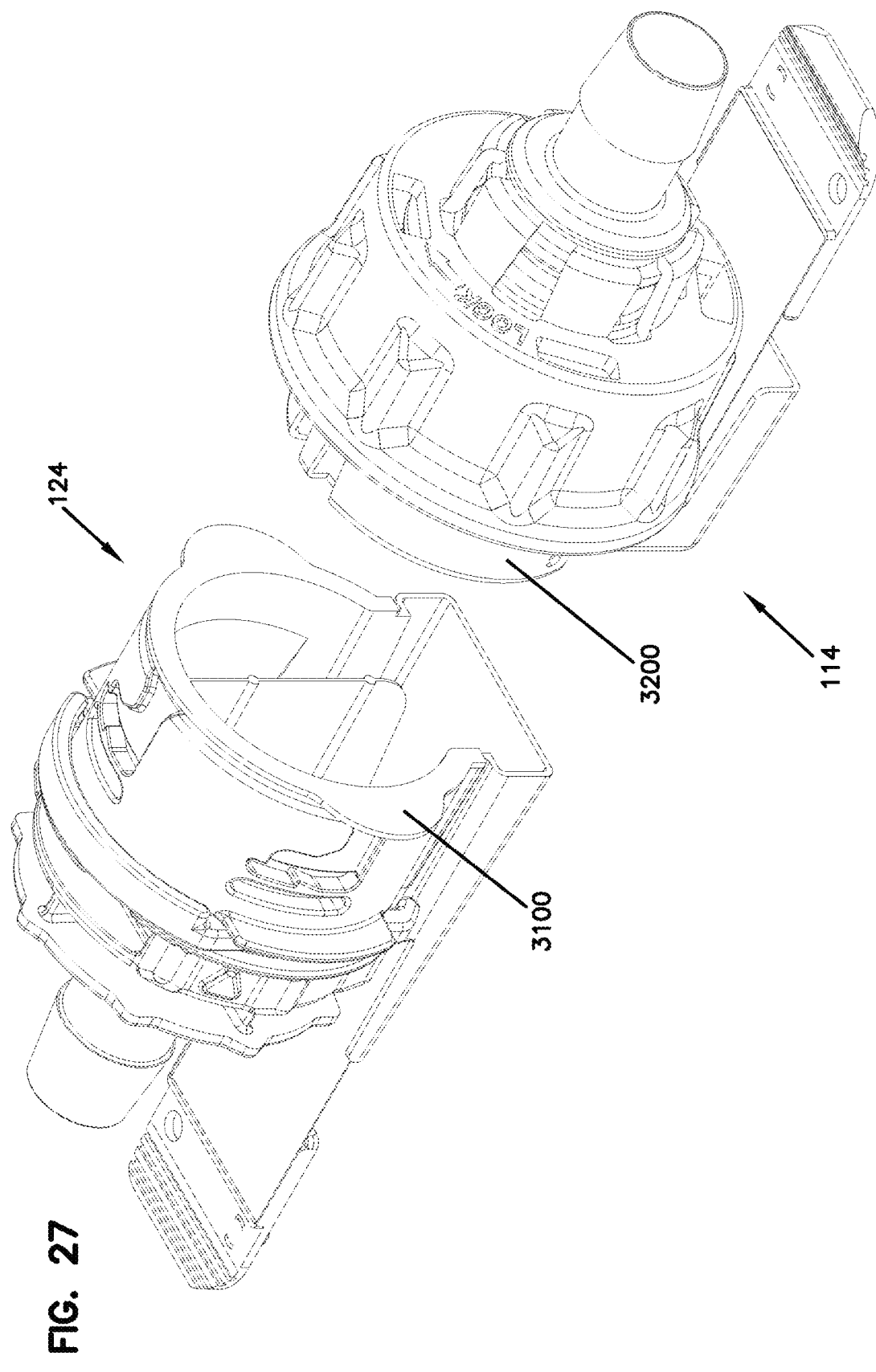
FIG. 27 is a second perspective view of the male and female aseptic coupling devices of FIG. 2 in an uncoupled state and with caps attached thereto.

Referring now to FIGS. 23-25, another example embodiment of an aseptic coupling arrangement 2124 is shown.

In this example, an aseptic coupling device 2152 includes a termination 2154 that is sized to be coupled to another coupling device, such as a quick disconnect coupler 1902. Examples of such couplers are described in U.S. Pat. Nos. D357,307; D384,731; 5,316,041; and 5,494,074. The entireties of these patents are hereby incorporated by reference. Other types of couplers can be used.

As shown, an insert member 2156 is connected (e.g., by sonic welding) to the termination 2154. The coupler 1902 is, in turn, connected to the insert member 2156.

In the example shown, the coupler 1902 includes a valving structure 1906, and the insert member 2156 includes a valving structure 2158. These valving structures 1906, 2158 are normally open when the coupler 1902 is connected to the insert member 2156, so that fluid can flow therethrough. In such an example, the entire device 2152 can be sterilized prior to use.

When fluid flow is complete, a latch 1908 of the coupler 1902 can be actuated to disconnect the coupler 1902 from the insert member 2156 positioned between the termination 2154 and the coupler 1902. When disconnected, valving structure 1906 in coupler 1920 stops the flow of fluid through the coupler 1920, and valving structure 2158 in the insert member 2156 stops the flow of fluid through the device 2124. This can result in a disconnect that is also aseptic. The coupler 1902 can thereupon, in turn, be connected to other terminations as desired.

In other embodiments, coupler 1902 can be connected to aseptic coupling device 114. In still further embodiments, both aseptic coupling devices 114 and 124 can each have a coupler connected thereto. In other examples, the coupler 1920 can be welded to the devices 114, 124, and the insert member 2156 can be coupled to the coupler 1920. Other configurations are possible.

Referring now to FIGS. 26-32, in example embodiments, a cap 3100 can be connected to aseptic coupling device 124, and a cap 3200 can be connected to aseptic coupling device 114. The caps 3100, 3200 function to protect the membranes 204, 206 prior to use. When ready for use, caps 3100, 3200 are removed from devices 114, 124 before devices 114, 124 are coupled.

Figure 28:
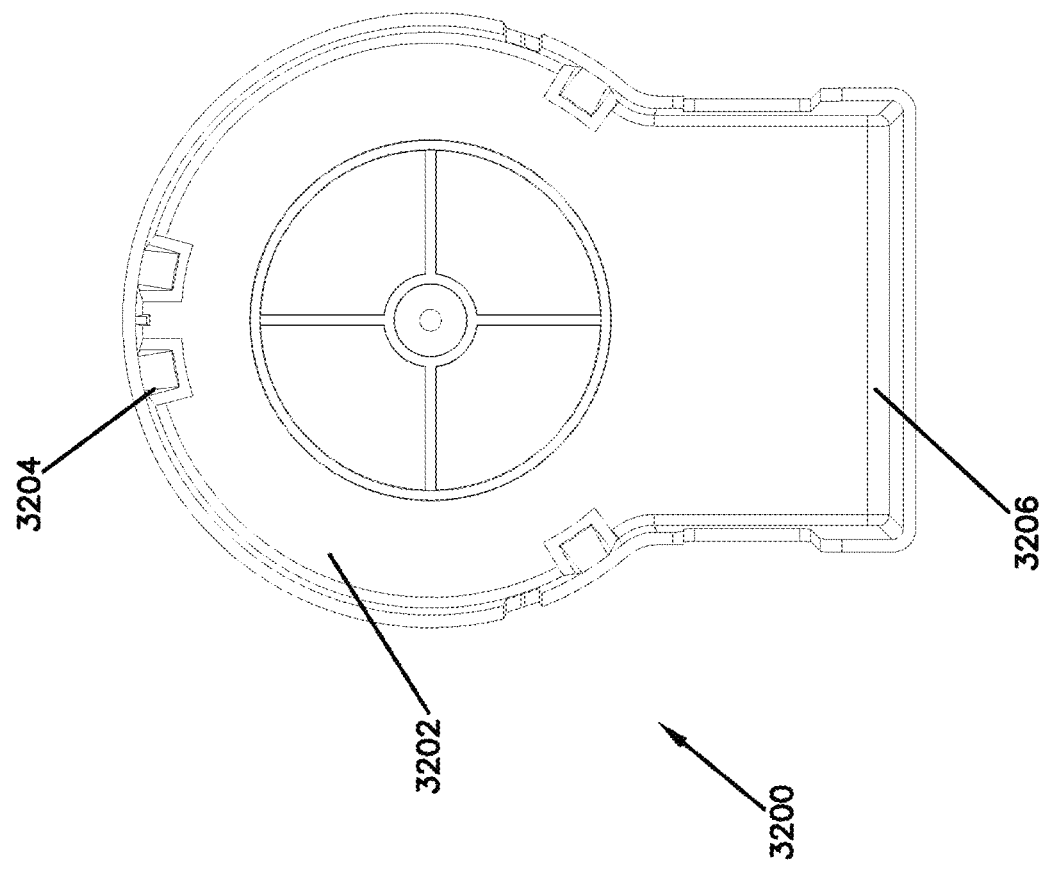
FIG. 28 is an end view of the cap of the male aseptic coupling device of FIG. 26.
Figure 29:
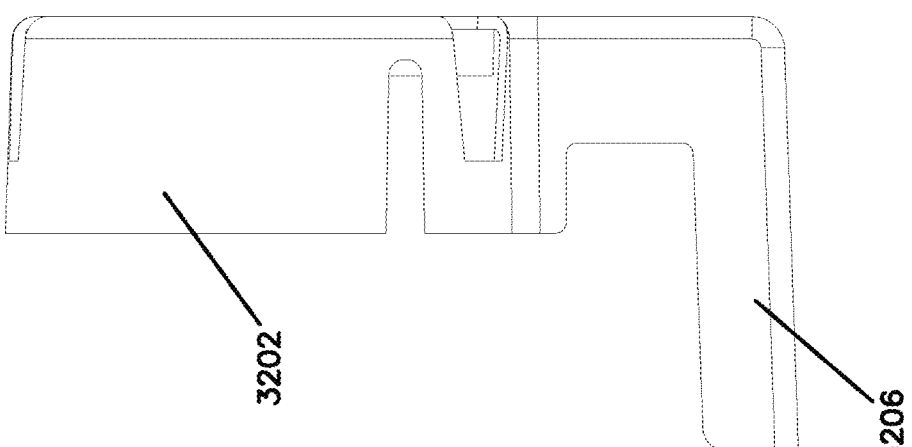
FIG. 29 is a side view of the cap of the male aseptic coupling device of FIG. 26.

As shown in FIGS. 28 and 29, the cap 3200 includes a body 3202 that is concave to surround the front surface 802 of inner member 201 of the device 114. Tabs 3204 on the body 3202 are received in the channel 304 on the inner member 201 to releasably couple the cap 3200 to the device 114. A bottom member 3206 guides and protects a lower portion of the membrane 204. The handle portion 520 attached to the member 204 extends out of the bottom member 3206.

Figure 30:
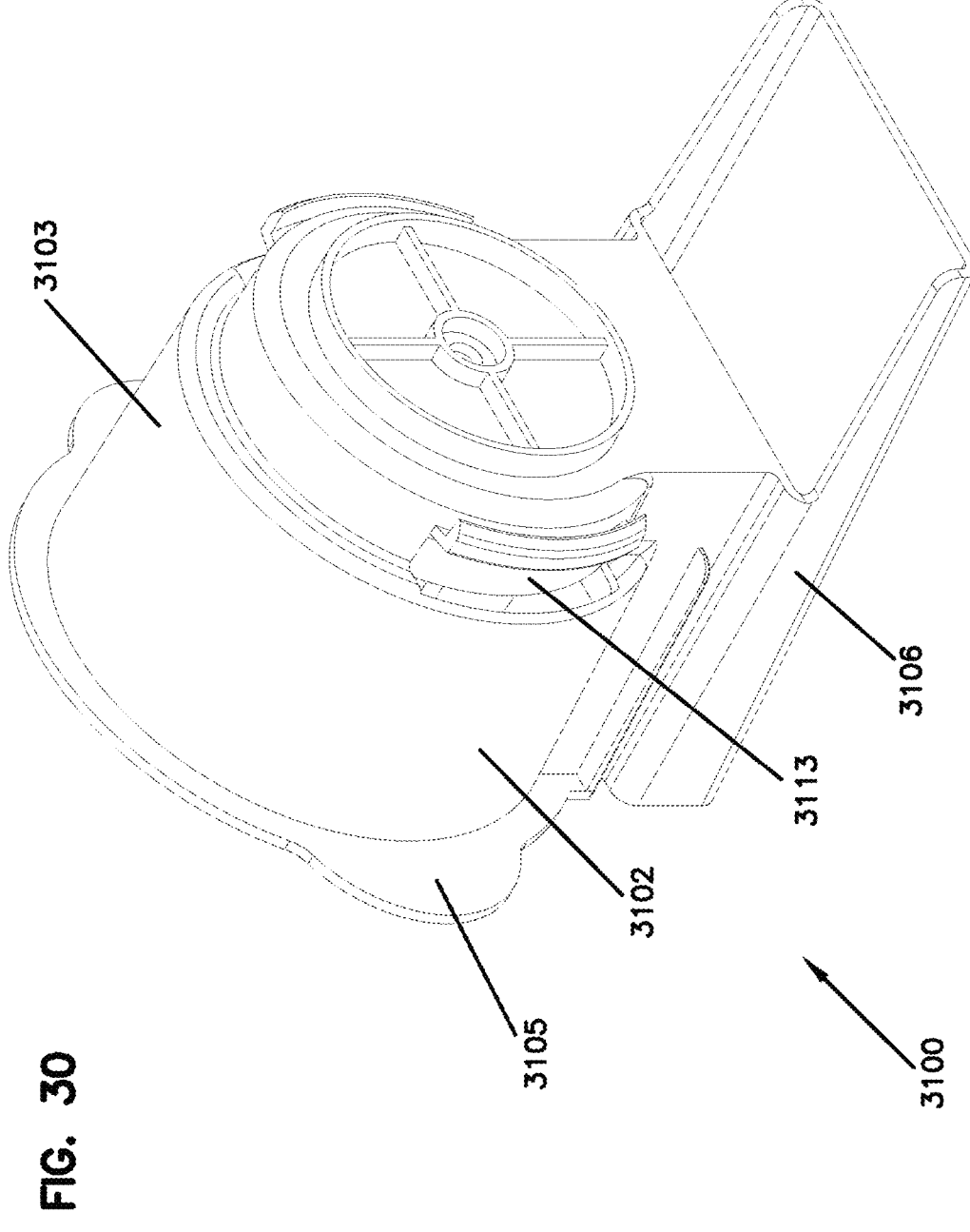
FIG. 30 is a perspective view of the cap of the female aseptic coupling device of FIG. 26.
Figure 31:
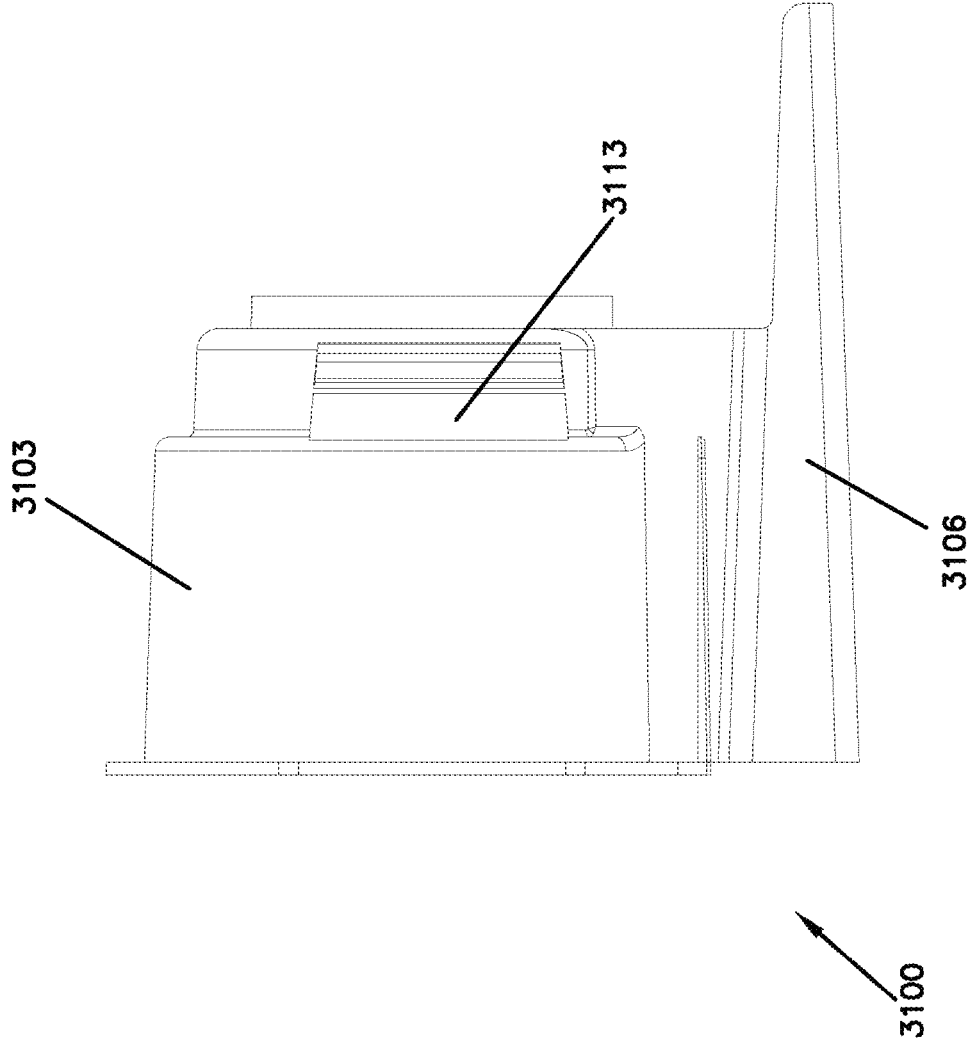
FIG. 31 shows a side view of the cap of the female aseptic coupling device of FIG. 26.
Figure 32:
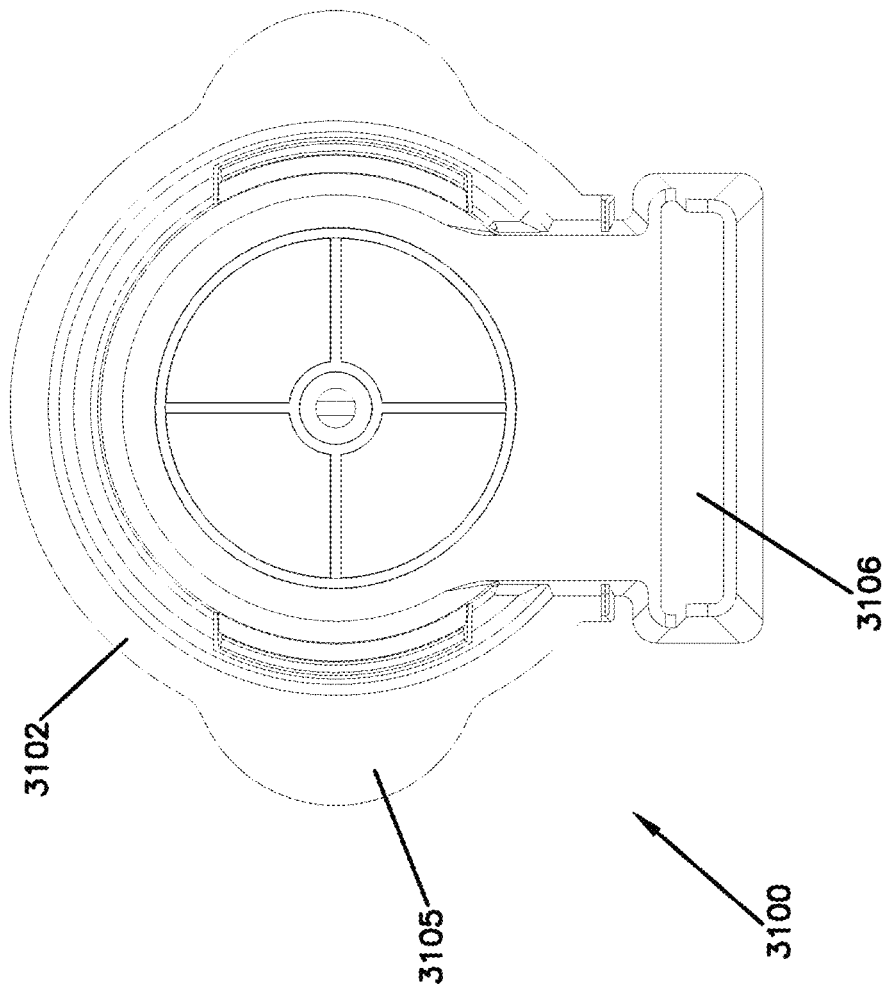
FIG. 32 is an end view of the cap of the female aseptic coupling device of FIG. 26.

As shown in FIGS. 30-32, the cap 3100 includes a body 3102 that extends into the device 124. Slots 3113 on each side of the body 3102 are positioned to engage ramped portions 1004 of the clip 212 (see FIG. 18) as the cap 3100 is inserted into the front portion 530 of the device 124 to releasably hold the cap 3100 to the device 124. Tabs 3105 formed on the body 3102 allow the user to grasp and remove the cap 3100 prior to use. A bottom member 3106 guides and protects a lower portion of the membrane 206. The handle portion 522 attached to the member 206 extends out of the bottom member 3106.

Figures 34, 35, 36:
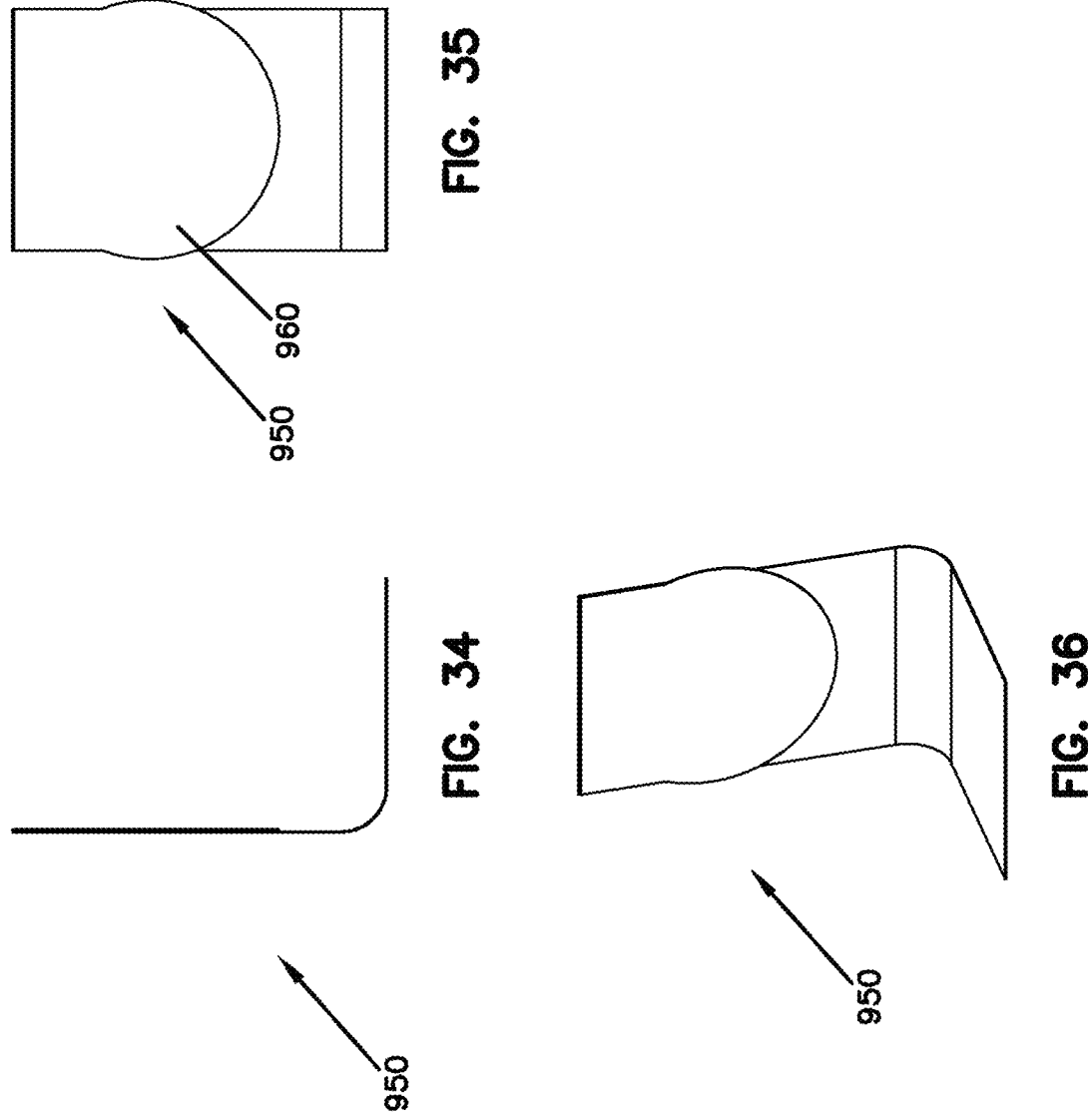
FIG. 34 is a side view of another example membrane for an aseptic coupling device.
FIG. 35 is a front view of the membrane of FIG. 34.
FIG. 36 is a perspective view of the membrane of FIG. 34.

Referring now to FIGS. 34-36, another example membrane 950 is shown. The membrane 950 is similar in construction to membranes 204, 206, and can be used in conjunction with either or both of the aseptic coupling devices 114, 124. In the example shown, the membrane 950 includes an enlarged portion 960 positioned at the end of the membrane 950 that is attached to the front surfaces 802, 910 of the devices 114, 124. Specifically, the enlarged portion 960 is spherical in shape so that the portion 960 generally encompasses a larger part of the front surface 802, 910 to provide a better sealing between the membrane 950 and the front surfaces 802, 910. Other configurations are possible.

In example embodiments, the aseptic coupling devices are made of a polymeric material. For example, in one embodiment, the aseptic coupling devices are made of polycarbonate and the seal members used therein are made of a silicone rubber. Other materials can be used.

In some embodiments, membranes 204, 206 are autoclavable and gamma stable for sterilization. In various embodiments, membranes 204, 206 are a composite design that consists of two components: 1 tag and 1 vent. The tag is a laminate including: a polyethylene terephthalate (PET) film, polyethylene (PE) foam, aluminum foil, and a sealing layer. The foam and/or foil may or may not exist in the final configuration. The sealing layer allows the tag to be bonded or welded to polycarbonate connectors (e.g., aseptic coupling devices 114 and 124). The vent is an expanded poly (tetrafluoroethylene) (ePTFE) membrane that will be bonded or welded onto the tag. Membranes 204, 206 are located over the center of the flow area of aseptic coupling devices 114 and 124, respectively, when the tags and vents are bonded or welded to connectors. The vent allows air and steam to flow into the system 100 during sterilization. The pore size of membranes 204, 206 are such that membranes 204, 206 filter out microorganisms larger than 0.2 microns.

In another embodiment, membranes 204, 206 are a polyethersulfone (PES) and polyester laminate membrane. This membrane is hydrophobic and breathable. The pore size is such that microorganisms larger than 0.2 microns are filtered out. When bonded, the polycarbonate melts into the polyester fibers, so that the PES acts as the filter, and the polyester acts as the structure.

In other embodiments, membranes 204, 206 are a Tyvek membrane that is coated on one side to allow membranes 204, 206 to be bonded to polycarbonate connectors (e.g., aseptic coupling devices 114 and 124). Tyvek is breathable in nature, so there is no need for an additional vent. Tyvek is a non-woven polyethylene membrane.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

The invention claimed is:

1. An aseptic coupling device, comprising:
   a member defining a fluid passage therethrough and including a front surface defining an opening;
   a seal member positioned in the opening; and
   a membrane comprising:
      bonded portions;
      a folded portion; and
      a tail portion extending from the folded portion to a free end and extending from the folded portion in a direction in which the tail portion is configured to be pulled to remove the membrane from the front surface,
   wherein the bonded portions of the membrane comprise a linear portion and a circular portion, and
   wherein the circular portion has more surface area than the linear portion.

2. The aseptic coupling device of claim 1, wherein the front surface defines two recesses between the linear portion and the circular portion.

3. The aseptic coupling device of claim 1, wherein the opening is defined within the circular portion.

4. The aseptic coupling device of claim 1, wherein the membrane is bonded to the front surface using an adhesive.

5. The aseptic coupling device of claim 1, wherein the member is sized to be coupled with a member of a mating aseptic coupling device to form a pre-coupled state.

6. The aseptic coupling device of claim 5, wherein, when the membrane is removed, the seal member engages a second seal member of the other aseptic device to form a coupled or semi-coupled state in which a sterile flow path is created between the aseptic device and the other aseptic device.

7. The aseptic coupling device of claim 1, wherein a fold of the folded portion is configured to roll across the opening as the membrane is pulled in the direction to remove the membrane from the front surface.

8. The aseptic coupling device of claim 1, further comprising a handle attached to the free end of the membrane.

9. The aseptic coupling device of claim 1, further comprising a cap releasably coupled to the member and arranged to protect the membrane.

10. The aseptic coupling device of claim 9, wherein the cap comprises a body that is concave to surround the front surface.

11. An aseptic coupling device, comprising:
a member defining a fluid passage therethrough and including a front surface defining an opening;
a seal member positioned in the opening; and
a membrane comprising:
  a bonded portion coupled to the front surface and covering the seal member;

10 a folded portion; and
a tail portion extending from the folded portion to a free end and extending from the folded portion in a direction in which the tail portion is configured to be pulled to remove the membrane from the front surface,
wherein the seal member has a cross-sectional shape that includes a concaved outer diameter.

12. The aseptic coupling device of claim 11, wherein the cross-sectional shape of the seal member includes a concaved inner diameter.

13. The aseptic coupling device of claim 12, wherein a radius of the concaved outer diameter is less than a radius of the concaved inner diameter.

14. The aseptic coupling device of claim 12, wherein a radius of the concaved outer diameter is unequal to a radius of the concaved inner diameter.

15. The aseptic coupling device of claim 11, wherein a portion of the seal member projects outward from the front surface.

16. The aseptic coupling device of claim 11, wherein the cross-sectional shape of the seal member is thinner at a middle portion of the seal member than at end portions of the seal member.

* * * * *